United States Patent
Hamann et al.

(10) Patent No.: US 6,992,102 B2
(45) Date of Patent: *Jan. 31, 2006

(54) BICYCLIC MODULATORS OF ANDROGEN RECEPTOR FUNCTION

(75) Inventors: Lawrence Hamann, Cherry Hill, NJ (US); David Augeri, Princeton, NJ (US); Chongqing Sun, East Windsor, NJ (US); Jeffrey A. Robl, Newtown, PA (US); Mark E. Salvati, Lawrenceville, NJ (US); Tammy Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

This patent is subject to a terminal disclaimer.

(21) Appl. No.: 10/685,020

(22) Filed: Oct. 14, 2003

(65) Prior Publication Data

US 2004/0092559 A1    May 13, 2004

Related U.S. Application Data

(62) Division of application No. 10/209,461, filed on Jul. 31, 2002, now Pat. No. 6,670,386.

(60) Provisional application No. 60/309,059, filed on Jul. 31, 2001.

(51) Int. Cl.
*A61K 31/40* (2006.01)
*C07D 207/00* (2006.01)

(52) U.S. Cl. ............... 514/423; 548/530; 548/531; 548/538

(58) Field of Classification Search ............ 548/530, 548/531, 538; 514/423
See application file for complete search history.

(56) References Cited

U.S. PATENT DOCUMENTS

| 3,948,933 | A | 4/1976 | Fontanella |
| 5,403,817 | A | 4/1995 | Seckinger et al. |
| 5,482,921 | A | 1/1996 | Seckinger et al. |
| 5,605,877 | A | 2/1997 | Schafer et al. |
| 2002/0058685 | A1 | 5/2002 | Hamilton |

FOREIGN PATENT DOCUMENTS

| AU | A-82875/87 | 6/1988 |
| EP | 0 272 594 A1 | 12/1987 |
| EP | 0 493323 B1 | 1/1992 |
| EP | 1 004 583 A3 | 5/2000 |
| GB | 1 503 244 | 3/1978 |
| WO | WO 00/13508 | 3/2000 |
| WO | WO 01/16108 A2 | 3/2001 |
| WO | WO 01/16133 A2 | 3/2001 |
| WO | WO 01/16139 A1 | 3/2001 |
| WO | WO 01/30781 A2 | 5/2001 |
| WO | WO 01/46195 A1 | 6/2001 |

OTHER PUBLICATIONS

Alexey B. Dyatkin, (1997) Tetrahedron Letters, vol. 28, No. 12, pp. 2065-2066.

I. Lalezari (1), S. Seifter and A. Thein (2), "Synthesis of 1H,3H-Imidazo[1,5-c]thiazole-5,7-[6H,7aH]-dione and 7,8-Dihydro-5H-imidazo[1,5-c][1,3]thiazine-1,3-[2H,8aH]-dione and Derivatives", Journal of Heterocyclic Chemistry, 20(2), pp. 483-485 (1983).

Uozumi, Y. et al., "A parallel preparation of a bicyclic N-chiral amine library and its use for chiral catalyst screening", Tetrahedron Letters 42, pp. 407-410 (2001).

Iseki, K. et al., "Asymmetric Allylation of Aromatic Aldehydes Catalyzed by Chiral Phosphoramides Prepared from (S)-Proline", Tetrahedron, vol. 53, No. 10, pp. 3513-3526 (1997).

*Primary Examiner*—Taofiq Solola
*Assistant Examiner*—Robert Shiao
(74) *Attorney, Agent, or Firm*—Sammy G. Duncan, Jr.; Maureen P. O'Brien

(57) ABSTRACT

The invention provides compounds of the formula I

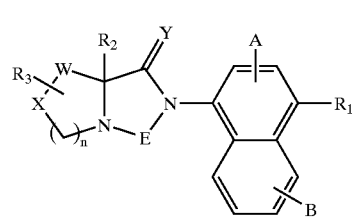

wherein the substitutents are as described herein.

Further provided are methods of using such compounds for the treatment of nuclear hormone receptor-associated conditions, such as age related diseases, for example sarcopenia, and also provided are pharmaceutical compositions containing such compounds.

3 Claims, No Drawings

BICYCLIC MODULATORS OF ANDROGEN RECEPTOR FUNCTION

CROSS-REFERENCE TO RELATED APPLICATIONS

This application is a divisional of application Ser. No. 10/209,461, filed Jul. 31, 2002 now U.S. Pat. No. 6,670,386, which claims the benefit of U.S. Provisional Application No. 60/309,059, filed Jul. 31, 2001, which are incorporated herein by reference.

FIELD OF THE INVENTION

The present invention relates to bicyclic compounds, methods of using such compounds in the treatment of androgen receptor-associated conditions, such as age related diseases, for example sarcopenia, and to pharmaceutical compositions containing such compounds.

BACKGROUND OF THE INVENTION

Nuclear hormone receptors (NHR's) constitute a large super-family of structurally-related and sequence-specific gene regulators scientists have named "ligand dependent transcription factors." R. M. Evans, Science, 240:889 (1988). The steroid binding NHR's (SB-NHR's) form a recognized subset of the NHR's, including the progesterone receptor (PR), androgen receptor (AR), estrogen receptor (ER), glucocorticoid receptor (GR) and mineralocorticoid receptor (MR). The conventional nuclear hormone receptors are generally transactivators in the presence of ligand, which selectively bind to the NHR in a way that effects gene transcription. In the absence of a corresponding ligand, some of the orphan receptors behave as if they are transcriptionally inert. Others, however, behave as either constitutive activators or repressors. These orphan nuclear hormone receptors are either under the control of ubiquitous ligands that have not been identified, or do not need to bind ligand to exert these activities.

The AR is a ligand-activated transcriptional regulatory protein that mediates induction of male sexual development and function through its activity with endogenous androgens. In addition, androgens are associated with male and female maintenance of muscle mass and strength, bone mass and erythropoiesis. Androgens, such as testosterone, also play an important role in many physiological processes, such as differentiation of male internal and external genitalia, development and maintenance of male secondary sexual characteristics (e.g., the development of prostate, seminal vesicles, penis, scrotum, skeletal muscle, redistribution of body fat, stimulation of long bone growth, closure of epiphyses, development of male hair growth pattern and enlargement of larynx), the maintenance of sexual behavior and function (e.g., libido and potency) and spermatogenesis (in man).

As one ages, the serum androgen concentration in the body declines. The age dependent decline in androgens is associated with changes in body composition for men and woman, such as lower percentage of muscle mass and an increase in body fat, e.g., sarcopenia. In this regard, modulation of the AR gene can have an impact on the physiological effects associated with androgen production. However, the effectiveness of known modulators of steroid receptors is often tempered by their undesired side-effect profile, particularly during long-term administration. For example, the administration of synthetic androgens has been associated with liver damage, prostate cancer, adverse effects on male sexual function and adverse effects associated with cardiovascular and erythropoietic function.

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic antagonist of the PR, which is utilized as a birth control agent (Vegeto et al., Cell 69: 703–713 (1992)). Flutamide is an example of an antagonist of the AR, which is utilized for the treatment of prostate cancer (Neri et al, Endo. 91, 427–437 (1972)). Tamoxifen is an example of a tissue specific modulator of the ER function, that is used in the treatment of breast cancer (Smigel J. Natl. Cancer Inst. 90, 647–648 (1998)). Tamoxifen can function as an antagonist of the ER in breast tissue while acting as an agonist of the ER in bone (Grese et al., Proc. Natl. Acad. Sci. USA 94, 14105–14110 (1997)). Because of the tissue selective effects seen for Tamoxifen, this agent, and agents like it, are referred to as tissue selective estrogen receptor modulator. In addition to synthetically derived non-endogenous ligands, non-endogenous ligands for NHR's can be obtained from food sources (Regal et al., Proc. Soc. Exp. Biol. Med. 223, 372–378 (2000) and Hempstock et al., J. Med. Food 2, 267–269 (1999)). The flavanoid phytoestrogens are an example of an unnatural ligand for SB-NHR's that are readily obtained from a food source such as soy (Quella et al., J. Clin. Oncol. 18, 1068–1074 (2000) and Banz et al., J. Med. Food 2, 271–273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's or through directed approaches using the available crystal structures of a variety of NHR ligand binding domains (Bourguet et al., Nature 375, 377–382 (1995), Brzozowski, et al., Nature 389, 753–758 (1997), Shiau et al., Cell 95, 927–937 (1998) and Tanenbaum et al., Proc. Natl. Acad. Sci. USA 95, 5998–6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in J. Med. Chem., 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

Accordingly, identification of compounds which have good specificity for one or more steroid receptors, but which have reduced or no cross-reactivity for other steroid or intracellular receptors, would be of significant value in the treatment of male and female hormone responsive diseases. There is, therefore, a need in the art for the identification of selective modulators of the steroid binding nuclear hormone receptors, particularly non-steroidal, non-toxic tissue selective androgen receptor modulators, which activate the androgen receptor in skeletal muscle while demonstrating limited or neutral effect on other androgen responsive (e.g., prostate) tissues.

SUMMARY OF THE INVENTION

In accordance with illustrative embodiments and demonstrating features of the present invention, compounds are provided which are capable of modulating the function of a nuclear hormone receptor. Preferably the compounds are selective androgen receptor modulators, and have the general formula I

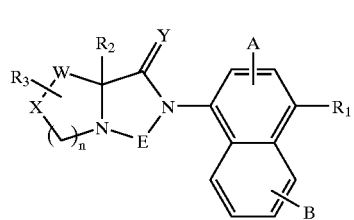

I wherein $R_1$ is selected from the group consisting of hydrogen (H), cyano (—CN), nitro (—$NO_2$), halo, heterocyclo, $OR_4$, $CO_2R_5$, $CONHR_5$, $COR_5$, $S(O)_mR_5$, $SO_2NR_5R_5'$, $NHCOR_5$ and $NHSO_2R_5$;

$R_2$ is selected from the group consisting of hydrogen (H), alkyl or substituted alkyl, alkenyl or substituted alkenyl, arylalkyl or substituted arylalkyl, $CO_2R_5$, $CONR_5R_5'$ and $CH_2OR_5$;

$R_3$ is selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, heterocycloalkyl or substituted heterocycloalkyl, aryl or substituted aryl, heteroaryl or substituted heteroaryl, halo, cyano (—CN), $NHCOR_5$, $NHCO_2R_5$, $NHCONR_5R_5'$, $NHSO_2R_5$ and $OR_4$;

$R_4$ in each functional group is independently selected from the group consisting of hydrogen (H), alkyl or substituted alkyl, $CHF_2$, $CF_3$ and $COR_5$;

$R_5$ and $R_5'$ in each functional group are each independently selected from the group consisting of hydrogen(H), alkyl or substituted alkyl, alkenyl or substituted alkenyl, alkynyl or substituted alkynyl, cycloalkyl or substituted cycloalkyl, heterocycloalkyl or substituted heterocycloalkyl, arylalkyl or substituted arylalkyl, aryl or substituted aryl, heteroaryl or substituted heteroaryl and —CN;

W is selected from the group consisting of $(CR_6R_6')_m$, $CHOH(CR_6R_6')_m$, $CO(CR_6R_6')_m$ and $C=NOR_4(CR_6R_6')_m$;

$R_6$ and $R_6'$ are each independently selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, heterocycloalkyl or substituted heterocycloalkyl, aryl or substituted aryl, heteroaryl or substituted heteroaryl, halo, cyano (—CN), $NHCOR_5$, $NHCO_2R_5$, $NHCONR_5R_5'$, $NHSO_2R_5$ and $OR_4$;

X is selected from the group consisting of methylene (—$CH_2$—), oxygen(O), $S(O)_m$, $NCOR_5$, $NCO_2R_5$, $NCONHR_5R_5'$ $NSO_2NR_5R_5'$;

Y is selected from the group consisting of oxygen(O), sulfur(S) and hydrogen ($H_2$);

E is selected from the group consisting of C=Z, $CHR_5$, $SO_2$, $P(O)R_5$ and $P(O)OR_5$;

Z is selected from the group consisting of oxygen(O), sulfur(S), NH and $NR_5$;

A and B are each independently selected from the group consisting of hydrogen (H), halo, cyano (—CN), nitro (—$NO_2$), alkyl or substituted alkyl and $OR_4$;

m is an integer from 0 to 2; and n is an integer of 1 or 2.

The definition of formula I above is inclusive of all prodrug esters, stereoisomers and pharmaceutically acceptable salts of formula I.

Further embodiments of the present invention include compounds of the formula Ia

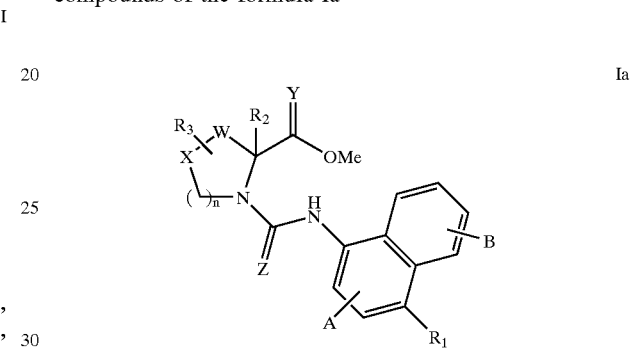

Ia wherein $R_1$ is selected from the group consisting of hydrogen (H), cyano (—CN), nitro (—$NO_2$), halo, heterocyclo, $OR_4$, $CO_2R_5$, $CONHR_5$, $COR_5$, $S(O)_mR_5$, $SO_2NR_5R_5'$, $NHCOR_5$ and $NHSO_2R_5$;

$R_2$ is selected from the group consisting of hydrogen (H), alkyl or substituted alkyl, alkenyl or substituted alkenyl, arylalkyl or substituted arylalkyl, $CO_2R_5$, $CONR_5R_5'$ and $CH_2OR_5$;

$R_3$ is selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, heterocycloalkyl or substituted heterocycloalkyl, aryl or substituted aryl, heteroaryl or substituted heteroaryl, halo, cyano (—CN), $NHCOR_5$, $NHCO_2R_5$, $NHCONR_5R_5'$, $NHSO_2R_5$ and $OR_4$;

$R_4$ in each functional group is independently selected from the group consisting of hydrogen (H), alkyl or substituted alkyl, $CHF_2$, $CF_3$ and $COR_5$;

$R_5$ and $R_5'$ in each functional group are each independently selected from the group consisting of hydrogen(H), alkyl or substituted alkyl, alkenyl or substituted alkenyl, alkynyl or substituted alkynyl, cycloalkyl or substituted cycloalkyl, heterocycloalkyl or substituted heterocycloalkyl, arylalkyl or substituted arylalkyl, aryl or substituted aryl, heteroaryl or substituted heteroaryl and —CN;

W is selected from the group consisting of $(CR_6R_6')_m$, $CHOH(CR_6R_6')_m$, $CO(CR_6R_6')_m$ and $C=NOR_4(CR_6R_6')_m$;

$R_6$ and $R_6'$ are each independently selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, heterocycloalkyl or substituted heterocycloalkyl, aryl or substituted aryl, heteroaryl or substituted heteroaryl, halo, cyano (—CN), NHCOR$_5$, NHCO$_2$R$_5$, NHCONR$_5$R$_5$', NHSO$_2$R$_5$ and OR$_4$;

X is selected from the group consisting of methylene (—CH$_2$—), oxygen(O), S(O)$_m$, NCOR$_5$, NCO$_2$R$_5$, NCONHR$_5$R$_5$' NSO$_2$NR$_5$R$_5$';

Y is selected from the group consisting of oxygen(O), sulfur(S) and hydrogen (H$_2$);

Z is selected from the group consisting of oxygen(O), sulfur(S), NH and NR$_5$;

A and B are each independently selected from the group consisting of hydrogen (H), halo, cyano(—CN), nitro (—NO$_2$), alkyl or substituted alkyl and OR$_4$;

m is an integer from 0 to 2; and n is an integer of 1 or 2.

The definition of formula Ia above is inclusive of all prodrug esters, stereoisomers and pharmaceutically acceptable salts of formula Ia.

The compounds of formula I and formula Ia modulate the function of nuclear hormone receptors, particularly the androgen receptor, and include compounds which are, for example, selective agonists, partial agonists, antagonists or partial antagonists of the androgen receptor. Preferably the compounds of formula I and Ia possess activity as agonists of the androgen receptor and may be used in the treatment of diseases or disorders associated with androgen receptor activity, such as maintenance of muscle strength and function (e.g., in the elderly); reversal or prevention of frailty or age-related functional decline ("ARFD") in the elderly (e.g., sarcopenia); prevention of catabolic side effects of glucocorticoids; prevention and treatment of reduced bone density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); acceleration of wound healing; accelerating bone fracture repair (such as accelerating the recovery of hip fracture patients); treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy.

The present invention provides for compounds of formula I and Ia, pharmaceutical compositions employing such compounds and for methods of using such compounds. In particular, the present invention provides a pharmaceutical composition comprising a therapeutically effective amount of a compound of formula I, Ia or both, alone or in combination with a pharmaceutically acceptable carrier.

Further, in accordance with the present invention, a method is provided for preventing, inhibiting or treating the progression or onset of diseases or disorders associated with nuclear hormone receptors, particularly, the androgen receptor, such as the diseases or disorders defined above and hereinafter, wherein a therapeutically effective amount of a compound of formula I, Ia or both, is administered to a mammalian, i.e., human, patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I, Ia or both, and another type of therapeutic agent, is administered to a human patient in need of treatment.

Preferred are compounds of formula I having the structure

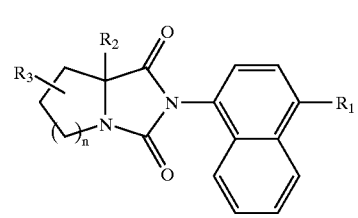

Ib

Especially preferred are compounds of formula Ib wherein:

R$_1$ is —NO$_2$, —CN or halogen;
R$_2$ is hydrogen or C$_1$–C$_3$ alkyl;
R$_3$ is hydrogen or hydroxyl (—OH); and
n is an integer of 1 or 2.

DETAILED DESCRIPTION OF THE INVENTION

The following abbreviations are employed herein:
Chiralpak®=Trademark of Chiral Technologies, Inc. Eaton, Pa.
DBU=1,8-diazabicyclo[5.4.0]undec-7-ene
Diaion® WA21J=polyamine resin from Supelco. Co. Bellefonte, Pa.
EtOAc=ethyl acetate
HPLC=high performance liquid chromatography
MeOH=methanol
MS or Mass Spec=mass spectrometry
YMC®=trademark of YMC Co, Ltd., Kyoto, Japan
AcOH=acetic acid
Boc=tert-butoxycarbonyl
Et$_3$N=triethylamine
DEAD=diethyl azodicarboxylate
DMF=N,N-dimethylformamide
DMPU=1,3-dimethyl-3,4,5,6-tetrahydro-2(1H)-pyrimidinone
LDA=lithium diisopropylamide
KOH=potassium hydroxide
Pd/C=palladium on activated charcoal
TFA=trifluoroacetic acid
THF=tetrahydrofuran
RT=room temperature
  m.p.=melting point
min=minute(s)
h or hr=hour(s)
L=liter
mL=milliliter
μL=microliter
g=gram(s)
mg=milligram(s)
mol=moles
mmol=millimole(s)
nM=nanomolar The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, isopropyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

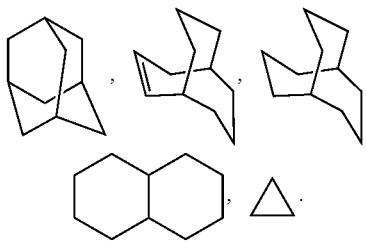

"Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the alkyl substituents.

Unless otherwise indicated, the term "alkenyl" or "lower alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3hexenyl, 2-heptenyl, 3-heptenyl, 4-heptenyl, 3-octenyl, 3-nonenyl, 4-decenyl, 3undecenyl, 4-dodecenyl, 4,8,12-tetradecatrienyl, and the like. "Substituted alkenyl" includes an alkenyl group optionally substituted with 1 or more substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the alkyl subs tituents set out herein.

Unless otherwise indicated, the term "alkynyl" or "lower alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. "Substituted alkynyl" includes an alkynyl group optionally substituted with one or more substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

Where alkyl groups as defined above have single bonds for attachment to other groups at two different carbon atoms, they are termed "alkylene" groups and may optionally be substituted as defined above for "alkyl".

The term "halogen" or "halo" as used herein alone or as part of another group refers to chlorine, bromine, fluorine, and iodine, with chlorine or fluorine being preferred.

The term "cyano," as used herein, refers to a —CN group.

The term "methylene," as used herein, refers to a —CH$_2$— group.

The term "nitro," as used herein, refers to a —NO$_2$ group.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

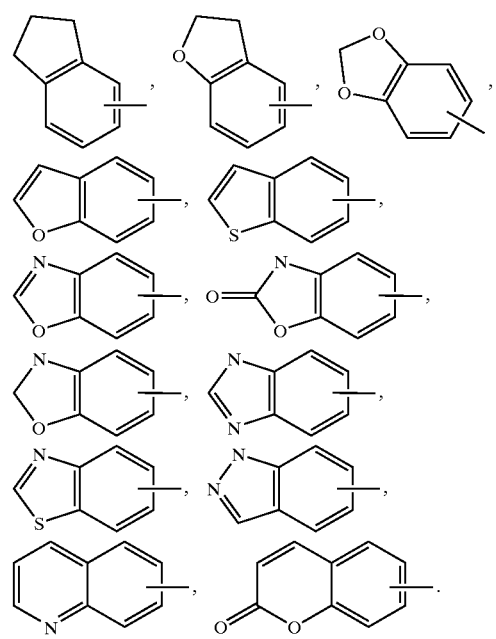

"Substituted aryl" includes an aryl group optionally substituted with 1 or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy; arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents such as any of the alkyl substituents set out above. Examples of heteroaryl groups include the following:

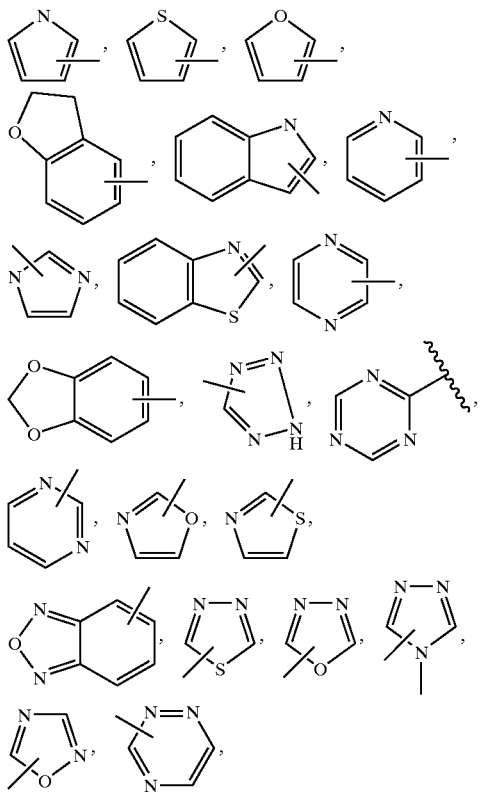

and the like.

The term "heterocyclo", heterocycle or heterocyclic ring, as used herein, represents an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The term "heterocycloalkyl" as used herein, represents a cycloalkyl group (nonaromatic) in which one or more of the carbon atoms in the ring is replaced by a heteroatom selected from O, S or N. "Substituted heterocycloalkyl" includes a heterocycloalkyl group optionally substituted with one or more substituents, such as any of the alkyl substituents set out above. Suitable heterocycloalkyls include, for example, piperazinyl, morpholinyl, tetrahydropyranyl, tetrahydrofuranyl, piperidinyl, pyrrolidinyl, oxazolinyl, and the like.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry*, Camille G. Wermuth et al., Ch 31, (Academic Press, 1996);

b.) *Design of Prodrugs*, edited by H. Bundgaard, (Elsevier, 1985);

c.) *A Textbook of Drug Design and Development*, P. Krogsgaard-Larson and H. Bundgaard, eds. Ch 5, pgs 113–191 (Harwood Academic Publishers, 199 1).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

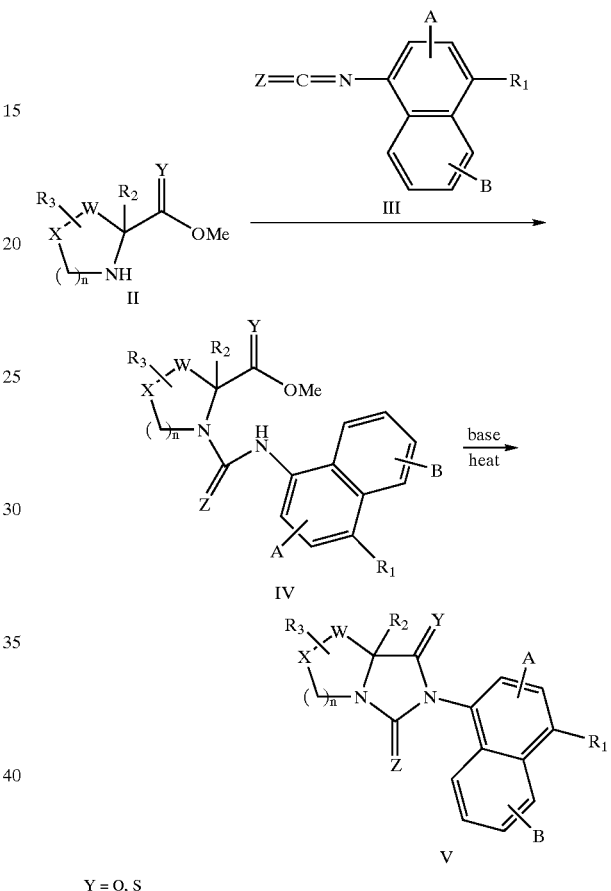

Scheme I

Y = O, S
Z = O, S, NH, NR$_5$

As illustrated in Scheme I, compounds of formula I can be prepared from suitably protected intermediates of formula II. Intermediates of formula II can be obtained commercially, can be prepared by methods known in the literature or can be readily prepared by one skilled in the art. Treatment of II with an intermediate of formula III yields an intermediate of formula of IV. The intermediates of formula III can be obtained, for example, from commercially available isocyanates, thioisocyanates and carbodiimides or can be readily prepared by one skilled in the art. The intermediate of formula IV can be heated with or without the presence of a base, such as DBU or triethylamine, to yield a compound of formula V. Compounds of formula V represent compounds of formula I wherein Y is O or S and E is C=Z. Compounds of formula V where X=S, can be converted to compounds where X=S(O)$_m$ with an oxidizing agent, such as 3-chloroperoxybenzoic acid. Compounds of formula V where X=NH, can be converted to compounds where X=NCOR$_5$, NCO$_2$R$_5$, NCONHR$_5$R$_5$' NSO$_2$NR$_5$R$_5$' by methods known in the literature or can readily prepared by one skilled in the art.

Scheme II

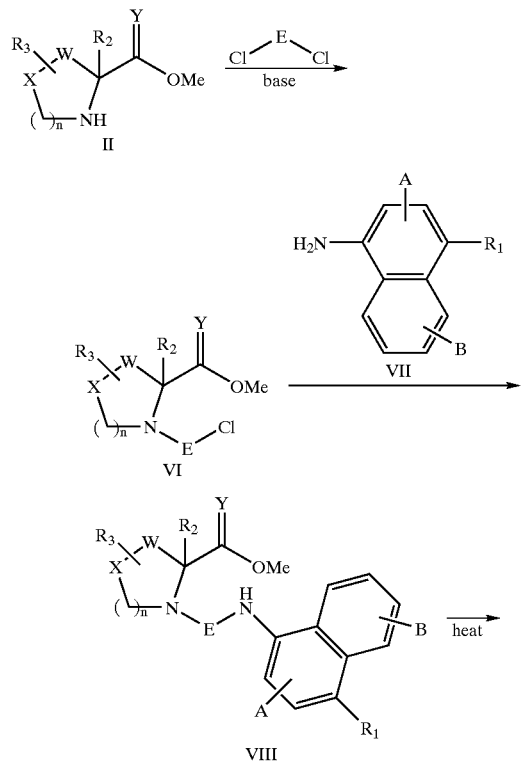

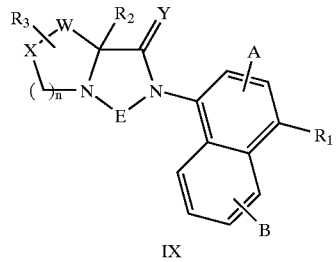

Y = O, S
E = C = Z, SO$_2$, P(O)R$_5$, P(O)OR$_5$,

Scheme II describes a method for preparing compounds of formula I wherein a suitably protected intermediate of formula II is treated with a phosgene like reagent of formula Cl-E-Cl in the presence of a base, such as NaHCO$_3$ or triethylamine, to yield an intermediate of formula VI. The phosgene like intermediates of formula Cl-E-Cl can be obtained from commercially available sources, can be prepared by methods known in the literature or can be readily be prepared by one skilled in the art. Phosgene equivalents such as carbonyldiimidazoles, may alternatively be substituted for Cl-E-Cl. The intermediate of formula VI can be reacted with an amine of formula VII. in the presence of a base, such as triethylamine, to give an intermediate of formula VIII. The amine intermediates VII can be obtained from commercially available sources, can be prepared by methods known in the literature or can be readily be prepared by one skilled in the art. Subsequently, the intermediate VIII can be converted to a compound of formula IX by heating with or without the presence of a base, such as DBU or triethylamine. The compound of formula IX represents compounds of formula I wherein Y is O or S and E is C=Z, SO$_2$, P(O)R$_5$, or P(O)OR$_5$.

Scheme III

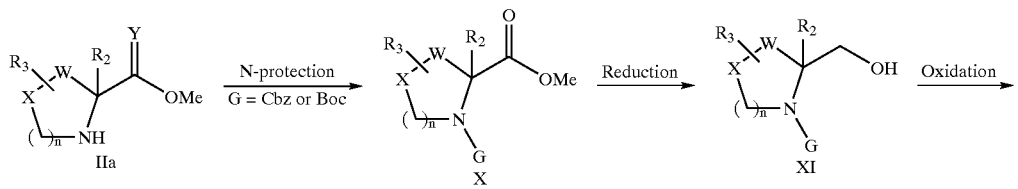

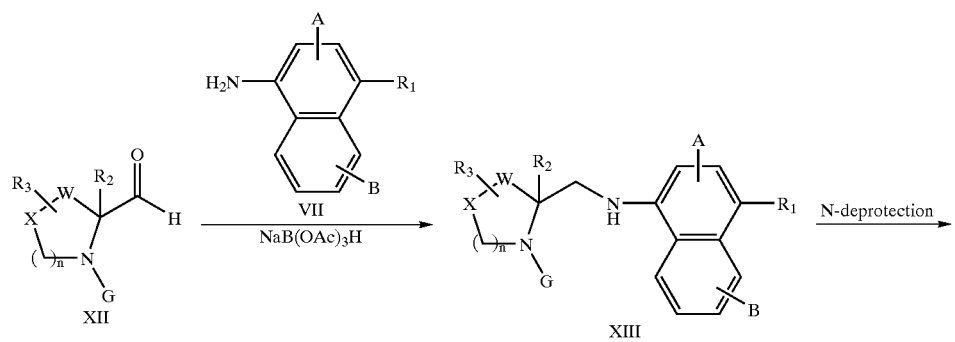

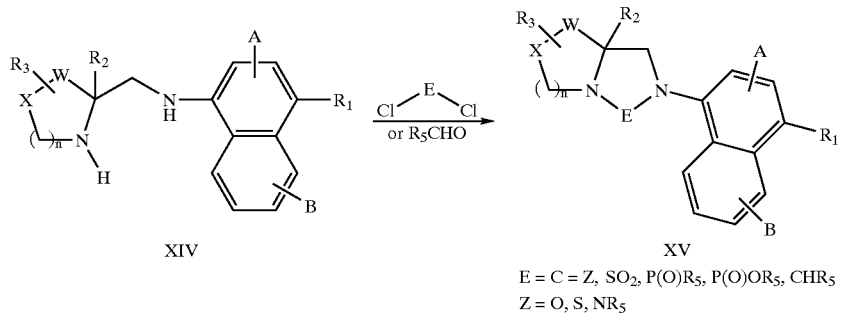

XIV $E = C = Z$, $SO_2$, $P(O)R_5$, $P(O)OR_5$, $CHR_5$
$Z = O$, $S$, $NR_5$

XV

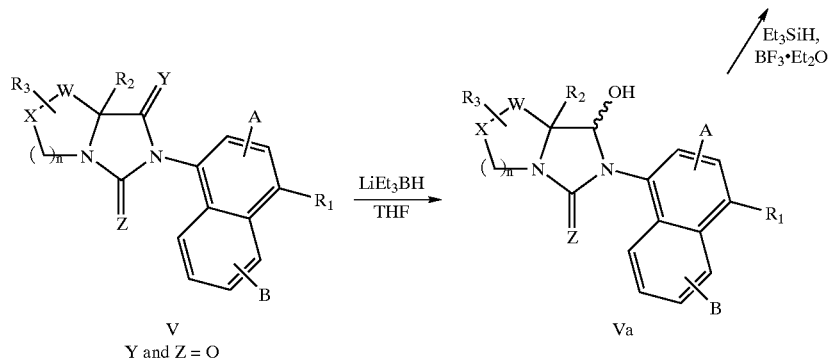

V
Y and Z = O

Va

Scheme III describes a method for preparing compounds of formula I wherein an intermediate of formula IIa is protected with an N-protecting group (G), such as Boc, to yield an N-protected intermediate of formula X. The intermediate of formula X can be treated with a reducing agent, such as lithium aluminum hydride, to form an alcohol intermediate XI, which can be oxidized to an aldehyde intermediate XII. The aldehyde XII can be reacted with an amine of formula VII (as described in Scheme II) in the presence of a reducing agent, such as sodium triacetoxyborohydride to give an intermediate of formula XIII. Removal of the N-protecting group (such as Boc) can be achieved by treatment of the intermediate of formula XIII with acid, such as hydrochloric acid in dioxane, or trifluoroacetic acid in methylene chloride, to provide an intermediate of formula XIV. The intermediate of formula XIV can be treated with reagents Cl-E-Cl (as described in Scheme II) in the presence of a base, such as triethylamine, to provide a compound of formula XV wherein E is C=Z, $SO_2$, $P(O)R_5$, $P(O)OR_5$. Alternatively, intermediate XIV can be treated with an aldehyde of formula $R_5CHO$, to provide a compound of formula XV wherein E is $CHR_5$. The compound of formula XV represents compounds of formula I wherein Y is $H_2$ and E is C=Z, $SO_2$, $P(O)R_5$, $P(O)OR_5$ or $CHR_5$.

Alternatively, a compound of formula V (as described in Scheme I) wherein Y and Z are oxygen (O) can be converted to an intermediate Va by a reducing agent, such as $LiEt_3BH$, preferably in a solvent such as THF at low temperature (<−40° C.). The intermediate Va can be subsequently treated with $Et_3SiH$ in the presence of boron trifluoride diethyl etherate in a solvent such as dichloromethane at low temperature (<0° C.) to furnish a compound of formula XV wherein E is C=Z and Z=O.

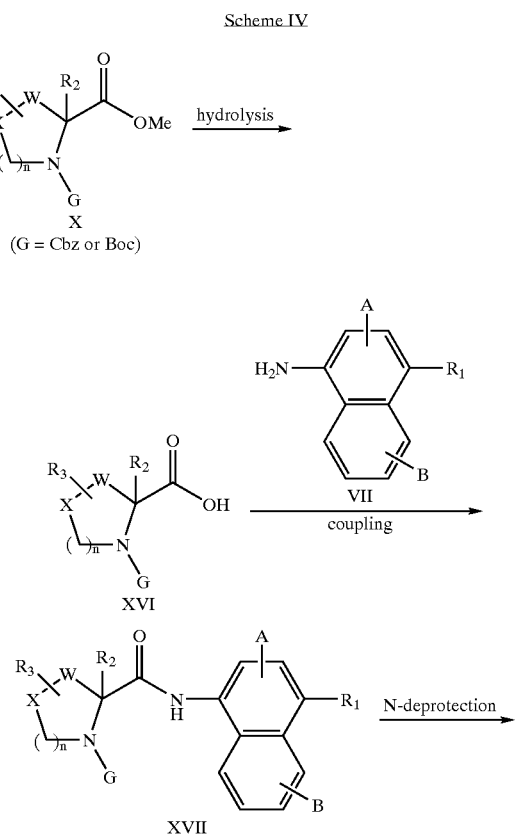

Scheme IV

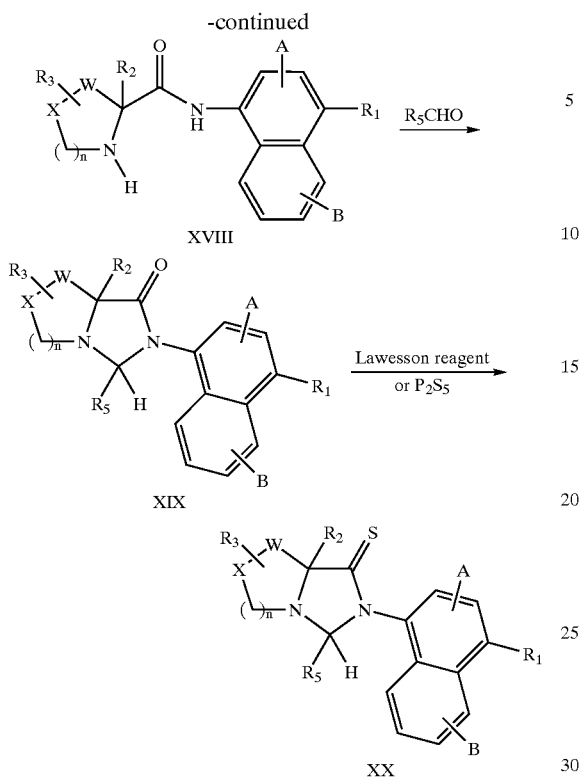

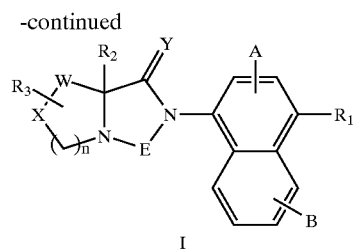

As illustrated in Scheme IV, an intermediate of formula X is saponified to an acid XVI by treatment with a base, such as lithium hydroxide. The acid XVI can be coupled to an amine VII via a variety of coupling reagents, for example, as described in "The practice of Peptide Synthesis" (Spring-Verlag, $2^{nd}$ Ed., Bodanszky, M. and Bodanszky, A.; 1993) to yield an amide intermediate of formula XVII. The intermediate of formula XVII is treated with an aldehyde ($R_5$CHO) in a suitable solvent (such as toluene), with or without the presence of a base, such as $K_2CO_3$, NaOH or DBU, or a weak acid, such as HOAc or p-toluenesulfulfonis acid, to give a compound of formula XIX. Aldehydes of formula $R_5$CHO can be obtained from commercially available sources, can be prepared by methods known in the literature or readily prepared by one skilled in the art. The compound of formula XIX represents compounds of formula I wherein Y is O and E is CHR$_5$. Alternatively, the compound of formula XIX can be treated with Lawesson reagent or $P_2O_5$ to give a compound of formula XX, which represents compounds of formula I where Y is S and E is CHR$_5$.

Scheme V

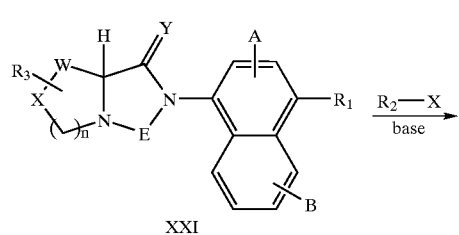

As illustrated in Scheme V, a suitably protected compound of formula XXI, which is a compound of formula I wherein $R_2$ is H, can be converted to a compound of formula I wherein $R_2$ a functional group other than H, as defined herein, by treatment with a base such as LDA and an alkyl halide such as iodomethane, preferably in a solvent such as THF at low temperatures (e.g., −78° C.) to yield a compound of formula I.

Scheme VI

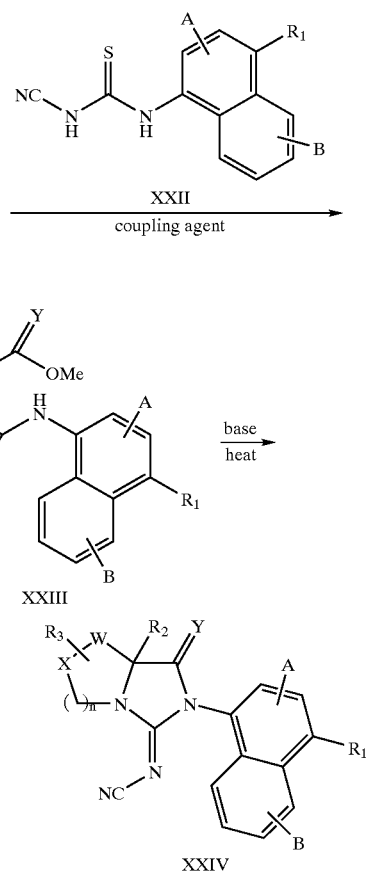

Y = O, S

Scheme VI illustrates a means to produce the compounds of formula I wherein E is C=Z and Z=N—CN. An intermediate of formula II is treated with a substituted cyano-thiourea of formula XXII, in the presence of a coupling agent, for example, as described in "The Practice of Peptide Synthesis" (Spring-Verlag, $2^{nd}$ Ed., Bodanszky, M. and Bodanszky, A.; 1993) to yield an intermediate of formula XXIII. The substituted cyano-thioureas of formula XXII can be obtained from commercially available sources, methods known in the literature or can readily be prepared by one skilled in the art. The intermediate of formula XXIII can be heated with or without the presence of a base, such as DBU, to yield a compound of formula XXIV, which represents a compound of formula I wherein E is C=N—CN.

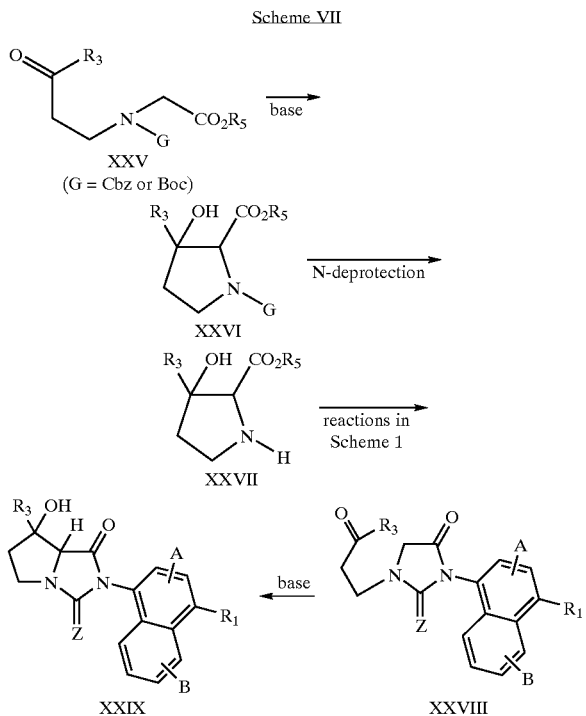

As illustrated in Scheme VII, proline derivatives of formula XXVI where $R_3$ is H or alkyl can be prepared by treatment of compounds of formula XXV with a base, such as potassium tert-butoxide in an aprotic solvent, such as toluene. Removal of the N-protection group (Cbz or Boc) can be achieved by methods known in the literature ("The Practice of Peptide Synthesis" (Spring-Verlag. $2^{nd}$ Ed., Bodanszky, M. and Bodanszky, A.; 1993). Compounds of formula XXIX can be prepared from intermediates XXVII following the reactions described in Scheme I. Alternatively, compounds of formula XXIX can also be prepared by treatment of intermediates XXVIII with a base, such as DBU in a suitable solvent such as toluene or dichloromethane.

Utility & Combinations

A. Utilities

The compounds of the present invention modulate the function of the nuclear hormone receptors, particularly the androgen receptor, and include compounds which are, for example, selective agonists, partial agonists, antagonists or partial antagonists of the androgen receptor (AR). Thus, the present compounds are useful in the treatment of AR-associated conditions. An "AR-associated condition," as used herein, denotes a condition or disorder which can be treated by modulating the function or activity of an AR in a subject, wherein treatment comprises prevention, partial alleviation or cure of the condition or disorder. Modulation may occur locally, for example, within certain tissues of the subject, or more extensively throughout a subject being treated for such a condition or disorder.

The compounds of the present invention can be administered to animals, preferably humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstural syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antibiotic or other pharmaceutically active material.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1–34) or bis-phosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

A further use of the compounds of this invention is in combination with progesterone receptor agonists ("PRA"), such as levonorgestrel, medroxyprogesterone acetate (MPA).

The compounds of the present invention may be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the, present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonins, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/

284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and phosphodiesterase-5 inhibitors (PDE-5 inhibitors) such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention may further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, B-hyroxy-B-methylbutyriate (Juven) and coenzyme Q-10.

In addition, compounds of the present invention may be used in combination with therapeutic agents used in the treatment of sexual dysfunction, including but not limited to PDE-5 inhibitors, such as sildenafil or IC-351.

Compounds of the present invention may further be used in combination with antiresorptive agents, hormone replacement therapies, vitamin D analogues, elemental calcium and calcium supplements, cathepsin K inhibitors, MMP inhibitors, vitronectin receptor antagonists, Src $SH_2$ antagonists, vacular —$H^+$-ATPase inhibitors, ipriflavone, fluoride, Tibolone, prostanoids, 17-beta hydroxysteroid dehydrogenase inhibitors and Src kinase inhibitors.

Compounds of the present invention may be used in combination with male contraceptives, such as nonoxynol 9 or therapeutic agents for the treatment of hair loss, such as minoxidil and finasteride or chemotherapeutic agents, such as with LHRH agonists.

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A–F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for an adult human of from about 0.01 to 2000 mg of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

Transactivation Assays

AR Specific Assay:

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.,* 271 (12): 7043–51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions −5322 and −3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA 453 cells were collected in media containing 10% charcoal stripped FBS. Each cell suspension was distributed into two Gene Pulser Cuvetts (Bio-Rad) which then received 8 □g of the reporter construct, and electoporated using a Bio-Rad Gene Pulser at 210 volts and 960 □Faraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from $10^{-10}$ to $10^{-5}$ M (sample). Duplicates were used for each sample. The compound dilutions were performed on a Biomek 2000 laboratory workstation.

After 48 hours, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

$$\% \text{ Inhibition} = 100 \times (1 - [\text{average control} - \text{average blank}/ \text{average sample} - \text{average blank}])$$

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay:

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM -0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45–99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_I$ values were determined by application of the Cheng-Prusoff equation to the $IC_{50}$ values, where:

$$K_1 = \frac{IC_{50}}{(1 + (^3\text{H-DHT})/K_d \text{ for } ^3\text{H-DHT})}.$$

After correcting for non-specific binding, $IC_{50}$ values were determined. The $IC_{50}$ is defined as the concentration of competing ligand needed to reduce specific binding by 50%. The $K_d$s for [$^3$H]-DHT for MDA 453 and LNCaP were 0.7 and 0.2 nM respectively.

Human Prostate Cell Proliferation Assay:

Compounds of the present invention were tested ("test compounds") on the proliferation of human prostate cancer cell lines. For that, MDA PCa2b cells, a cell line derived from the metastasis of a patient that failed castration, Navone et al., Clin. Cancer Res., 3, 2493–500 (1997), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]Thymidine incorporation was quantified (IC$_{50}$).

C2C12 Mouse Myoblast Transactivation Assay:

Two functional transactivation assays were developed to assess the efficacy of androgen agonists in a muscle cell background using a luciferase reporter. The first assay (ARTA Stable 1) uses a cell line, Stable 1 (clone #72), which expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. The Journal of Biological Chemistry 272, 8227–8235, (1997). It was developed by random mutagenesis of an AR/GR consensus enhancer sequence.

ARTA Stable 1:
1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1X MEM Na Pyruvate (Gibco BRL, Cat. No.: 11360-070), 0.5X Antibiotic-Antimycotic, and 800 µg/ml Geneticin (Gibco BRL, Cat. No.: 10131-035).
2. 48 hours later, cells are transfected with pGL3/2XDR-1/luciferase using LipofectAMINE Plus® Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 □l/well Opti-MEMem media (Gibco BRL, Cat. No.: 31985-070). To this, 0.5 □l/well Plus reagent is added. This mixture is incubated for 15 minutes at room temperature. In a separate vessel, 0.385 µl/well LipofectAMINE reagent is diluted with 5 □l/well Opti-MEM. The DNA mixture is then combined with the LipofectAMINE mixture and incubated for an additional 15 minutes at room temperature. During this time, the media from the cells is removed and replaced with 60 □l/well of Opti-MEM. To this is added 10 □l/well of the DNA/LipofectAMINE transfection mixture. The cells are incubated for 4 hours.
3. The transfection mixture is removed from the cells and replaced with 90 µl of media as in #1 above.
4. 10 µl/well of appropriate drug dilution is placed in each well.
5. 24 hours later, the Steady-Glo™ Luciferase Assay System is used to detect activity according to the manufacturer's instructions (Promega, Cat. No.: E2520).

ARTA Stable 2:
1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1X MEM Na Pyruvate (Gibco BRL, Cat. No.: 11360-070), 0.5X Antibiotic-Antimycotic, 800 µg/ml Geneticin (Gibco BRL, Cat. No.: 10131-035) and 800 µg/ml Hygromycin P (Gibco BRL, Cat. No.: 10687-010).
2. 48 hours later, the media on the cells is removed and replaced with 90 µl fresh. 10 µl/well of appropriate drug dilution is placed in each well.
3. 24 hours later, the Steady-Glo™ Luciferase Assay System is used to detect activity according to the manufacturer's instructions (Promega, Cat. No.: E2520).

PROLIFERATION ASSAYS

Murine Breast Cell Proliferation Assay:

The ability of compounds of the present invention ("test compounds") to modulate the function of the AR was determined by testing said compounds in a proliferation assay using the androgen responsive murine breast cell line derived from the Shionogi tumor, Hiraoka et al., Cancer Res., 47, 6560–6564 (1987). Stable AR dependent clones of the parental Shionogi line were established by passing tumor fragments under the general procedures originally described in Tetuo, et. al., Cancer Research 25, 1168–1175 (1965). From the above procedure, one stable line, SC114, was isolated, characterized and utilized for the testing of example compounds. SC114 cells were incubated with or without the test compounds for 72 hours and the amount of [3H]-thymidine incorporated into DNA was quantified as a surrogate endpoint to assess the number of cells and therefore the proliferation rate as described in Suzuki et. al., J. Steroid Biochem. Mol. Biol. 37, 559–567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi of [3H]-Thymidine (Amersham) was added per well and incubated for another 2 hr followed by tripsinization, and harvesting of the cells onto GF/B filters. Micro-scint PS were added to the filters before counting them on a Beckman TopCount.

For the antagonist mode, the % Inhibition was calculated as:

% Inhibition=100×(1−[average$_{sample}$−average$_{blank}$/average$_{control}$−average$_{blank}$])

Data was plotted and the concentration of compound that inhibited 50% of the [$^3$H]Thymidine incorporation was quantified (IC$_{50}$).

For the agonist mode % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

In Vitro Assay to Measure GR Induced AP-1 Transrepression:

The AP-1 assay is a cell based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5mg/ml geneticin. Cells are plated the day before the assay at approximately 40000 cells/well. On assay day, the media is removed by aspiration and 20 μl assay buffer (RPMI without phenol red+10% FCS (charcoal-treated)+Pen/Strep) is added to each well. At this point either 20 μl assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 μl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of ≦10 □M typically suppresses activity by 65%. Test compounds which demonstrate an inhibition of PMA induction of 50% or greater at a concentration of test compound of ≦10 □M are deemed active.

Levator Ani & Wet Prostate Weight Assay AR Agonist Assay:

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.*, 83, 175 (1953); B. L. Beyler et al, "Methods for evaluating anabolic and catabolic agents in laboratory animals", *J. Amer. Med. Women's Ass.*, 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.—Soc. Ital. Biol. Sper.* 42, 1596 (1966); Z. Gori et al., "Testosterone hypertrophy of levator ani muscle of castrated rats. II. Electron-microscopic observations" *Boll.—Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200–250 g, 6–8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7–14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Superanova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188–191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The EC$_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

The following examples serve to better illustrate, but not limit, some of the preferred embodiments of the invention.

EXAMPLE 1

Tetrahydro-2-(4-nitro-1-naphthalenyl)imidazo[1,5-α]pyridine-1,3(2H,5H)-dione

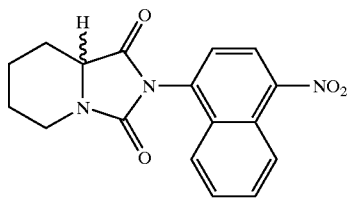

1A. 4-Nitro-1-naphthaleneisocyanate

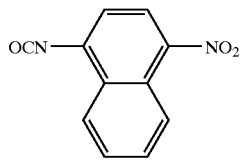

To a yellow solution of 1-amino-4-nitronaphthalene (5.17 g, 27.5 mmol) in CH$_2$Cl$_2$ (80 mL) was added solid NaHCO$_3$ (23.10 g, 275 mmol). The resulting suspension was stirred at 0° C. for 15 min, then phosgene (20%) in toluene (110 mmol) was added rapidly to the suspension. After addition, the mixture was stirred at RT for 2 hours, then filtered to remove the solid. The filtrate was concentrated under reduced pressure, the resulting solid residue dried in vacuo for 1 hour to give approximately 6.0 g of the title compound as a brown solid.

1B. Tetrahydro-2-(4-nitro-1-naphthalenyl)imidazo[1,5-α]pyridine-1,3(2H,5H)-dione To a solution of ethyl pipecolinate (0.234 g, 1.49 mmol) and compound 1A (0.29 g, 1.355 mmol) in toluene (6 mL) was added 4 Å molecular sieves (1.0 g). The mixture was stirred at room temperature overnight, filtered. The filtrate was diluted with EtOAc, washed with 1 N HCl, water, brine, dried over MgSO$_4$, concentrated under reduced pressure to give a brow colored foam, which was chromatographed (silica gel) eluting with CH$_2$Cl$_2$, 0.3% MeOH in CH$_2$Cl$_2$ to give 110 mg of the title compound (racemate) as a yellow solid. mp. 190–192° C.; HPLC: 100% at 2.64 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 326 [M+1]$^+$.

EXAMPLE 2

Tetrahydro-2-(4-nitro-1-naphthalenyl)-1H-pyrrolo[1,2-c]imidazole-1,3(2H)-dione

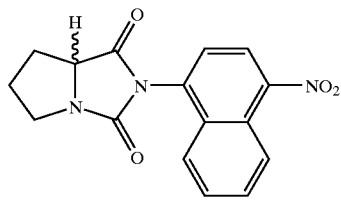

2A. (2S)-1-[[(4-nitro-1-naphthalenyl)amino]carbonyl]-2-pyrrolidinecarboxylic acid methyl ester

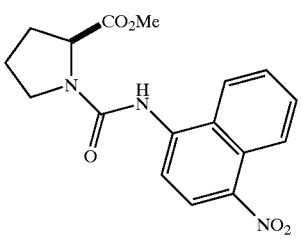

To a solution of L-proline methyl ester hydrochloride (257 mg, 1.43 mmol) in MeOH was added triethylamine (0.2 mL, 1.43 mmol). The solution was concentrated under reduced pressure to give a white solid residue, which was triturated with ether (3×). The collected ether solution was concentrated under reduced pressure to give L-proline methyl ester free amine (220 mg) as a colorless oil. To a solution of above free amine in toluene (5 mL) was added compound 1A (278 mg, 1.3 mmol), followed by 4 Å molecular sieves (1.0 g). The mixture was stirred at room temperature overnight and filtered. The filtrate was diluted with EtOAc, washed with 1 N aqueous HCl, water, brine, dried over MgSO$_4$, concentrated under reduced pressure to give a crude product, which was chromatographed (silica gel) eluting with CH$_2$Cl$_2$, 0.5% MeOH in CH$_2$Cl$_2$ to give the title compound (410 mg, 92% yield) as a yellow foam.

2B. Tetrahydro-2-(4-nitro-1-naphthalenyl)-1H-pyrrolo[1,2c]imidazole-1,3(2H)-dione A suspension of compound 2A (410 mg, 1.29 mmol) and DBU (0.2 mL, 1.33 mmol) in toluene (10 mL) was heated at 80° C. for 2 hours. HPLC check of the reaction showed little product formed. Additional DBU (0.1 mL) was added and the reaction heated at 90° C. overnight. After cooling to RT, the reaction mixture was filtered. The filtrate was diluted with EtOAc, washed with 1 N aqueous HCl, water, brine, dried over MgSO$_4$ and concentrated under reduced pressure to give a crude product, which was chromatographed (silica gel) eluting with CH$_2$Cl$_2$, 0.2% to 0.4% MeOH in CH$_2$Cl$_2$ to give the title compound (racemate) (80 mg) as a brown solid. mp. 215–217 C.°. HPLC: 97.5% at 2.51 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 312 [M+1]$^+$.

EXAMPLE 3

(6S)-Tetrahydro-6-hydroxy-2-(4-nitro-1-naphthalenyl)-1H-pyrrolo [1,2c]imidazole-1,3(2H)-dione

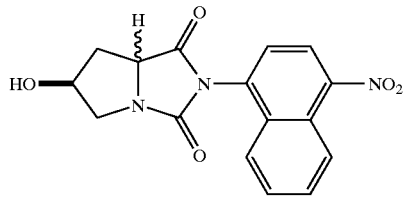

cis-4-Hydroxy-L-proline methyl ester hydrochloride salt (107 mg, 0.59 mmol) in MeOH was treated with triethylamine (82 μL). The solution was concentrated under reduced pressure and the resulting residue triturated with ether (3×50 mL). The combined ether extracts were concentrated under reduced pressure to give the amino acid ester as a free amine, which was suspended in toluene (10 mL) and compound 1A (126 mg, 0.59 mmol) was added, followed by 4 Å molecular sieves (~1.0 g). The mixture was stirred at RT until compound 1A was consumed (~2 hours). DBU (90 μL, 0.59 mmol) was added, the resulting dark-red colored suspension was heated at 67 C.° for 2 hours. The reaction mixture was cooled to RT and filtered. The filtrate was diluted with EtOAc, washed with saturated aqueous NH$_4$Cl, water, brine, dried over MgSO$_4$ and concentrated under reduced pressure to give a crude product, which was chromatographed (silica gel) eluting with 0.2% MeOH in EtOAc/hexane (7:3) to give the title compound (140 mg, 73% yield) as a yellow solid. mp. 249–251 C.°. HPLC: 99% at 2.13 to 2.28 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 328 [M+1]$^+$.

EXAMPLE 4

(6R)-Tetrahydro-6-hydroxy-2-(4-nitro-1-naphthalenyl)-1H-pyrrolo [1,2c]imidazole-1,3(2H)-dione

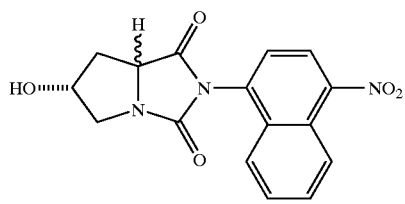

The title compound was prepared from trans-4-hydroxy-L proline methyl ester hydrochloride salt by the procedures analogous to those described in Example 3. mp. 246–248 C.°. HPLC: 99% at 2.16 to 2.31 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 328 [M+1]$^+$.

EXAMPLE 5

(6R)-Tetrahydro-2-(4-nitro-1-naphthalenyl)-6-(phenylmethoxy)-1H-pyrrolo[1,2-c]imidazole-1,3(2H)-dione

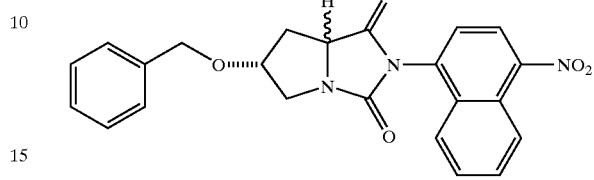

The title compound was prepared from trans-4-benzyloxy-L proline methyl ester hydrochloride salt by the procedures analogous to those described in Example 3. mp. 120–122 C.°. HPLC: 99% at 3.307 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 418 [M+1]$^+$.

EXAMPLE 6 trans-4-(Tetrahydro-7-hydroxy-1,3-dioxo-1H-pyrrolo[1,2c]-1imidazol-2(3H)-yl)-1-naphthalenecarbonitrile

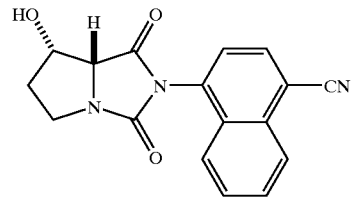

6A. (2S,3S)-3-Hydroxy-2-pyrrolidinecarboxylic acid methyl ester

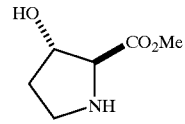

Hydrogen chloride gas was bubbled through a suspension of trans-3-hydroxy-L-proline (8 g, 61 mmol) in MeOH (800 mL) cooled at 0 C.° for 10 minutes. The resulting clear solution was stirred at RT for 2 hours. The reaction mixture was concentrated under reduced pressure, and obtained residue stripped with toluene, dried in vacuo to yield 12 g of the product as a HCl salt. To a solution of above ester HCl salt in MeOH was added 26 g of Diaion® WA21J resin (pre-washed with MeOH). The resulting suspension was stirred at RT for 30 minutes, then filtered. The filtrate was concentrated under reduced pressure to give the title compound as a colorless oil.

6B. 4-Cyano-1-naphthaleneisocyanate

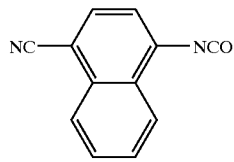

The title compound was prepared from 4-amino-1-naphthalenecarbonitrile in a similar fashion as that described in Example 1A.

6C. trans-4-(Tetrahydro-7-hydroxy-1,3-dioxo-1H-pyrrolo[1,2c]imidazol-2(3H)-yl)-1-naphthalenecarbonitrile To a suspension of 6B (5.35 g, 27.5 mmol) in toluene (500 mL) was added compound 6A (4.0 g, 27.5 mmol), followed by 4 Å molecular sieves (~10 g). The resulting mixture was stirred at RT overnight, then DBU (4.2 mL, 27.5 mmol) was added. The resulting dark-red colored suspension was heated at 76 C.° for 2 hours, then cooled at RT and filtered. The filtrate was diluted with EtOAc, washed with saturated aqueous $NH_4Cl$, water, brine, dried over $MgSO_4$, concentrated under reduced pressure to give a crude product, which was chromatographed (silica gel) eluting with EtOAc/hexane (1:1), 0.2 to 0.5% MeOH in EtOAc/hexane (1:1) to give 3.8 g of the title compound (racemate) as a beige colored solid. mp. 224–225 C.°. HPLC: 99% at 2.03 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 308 $[M+1]^+$

EXAMPLE 7

(7R,7αS)-4-(Tetrahydro-7-hydroxy-1,3-dioxo-1H-pyrrolo[1,2c]imidazol-2(3H)-yl)-1-naphthalenecarbonitrile

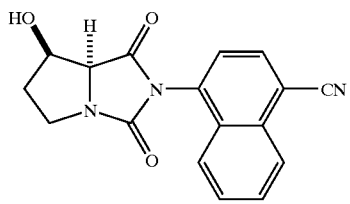

The title compound (1.77 g) was isolated from 6C (5.8 g) by using preparative HPLC with a chiral column (CHIRALPAK® AD, 5×50 cm, 20μ) and 25% of isopropanol/hexane as an eluate. mp. 229–230 C.°; $[\alpha]_D^{rt} = -29.76$; HPLC: 99% at 12.43 min (retention time) (CHIRALPAK® OD column 4.6×250 mm; 30% isopropanol in hexane over 20 minutes, 1 mL/min, monitoring at 220 nM); MS (ES): m/z 308 $[M+1]^+$ The title compound was also prepared by using a homochiral synthesis described below.

7A. (2S,3S)-N-tert-Butoxycarbonyl-3-hydroxy-2-pyrrolidinecarboxylic acid methyl ester

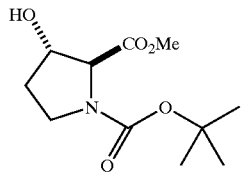

Hydrogen chloride gas was bubbled through a suspension of trans-3-hydroxy-L-proline (10 g, 76 mmol) in MeOH (300 mL) cooled at 0 C.° for 10 minutes. The resulting clear solution was stirred at RT for 2 hours. The reaction mixture was concentrated under reduced pressure, the resulting residue stripped with toluene and dried in vacuo to yield 14 g of methyl ester hydrochloride salt as a white solid. To a suspension of 11 g of the above ester hydrochloride salt in $CH_2Cl_2$ (300 mL) at RT was added $Et_3N$ (16.8 mL), followed by addition of di-tert-butyl dicarbonate (13.2 g) in portions. The mixture was stirred at RT for 3 hours, then partitioned between water and $CH_2Cl_2$. The organic phase was washed with saturated aqueous $NaHCO_3$ and brine, dried over $Na_2SO_4$ and filtered. The filtrate was concentrated under reduced pressure to give a crude product, which was chromatographed (silca gel) eluting with 50% EtOAc/hexane to give 13.6 g of the title compound as a colorless oil.

7B. (2S,3R)-N-tert-Butoxycarbonyl-3-benzoyloxy-2-pyrrolidinecarboxylic acid methyl ester

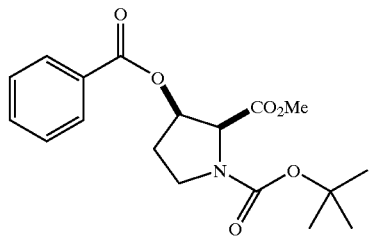

To a solution of 7A (13.5 g, 55 mmol) in anhydrous THF (500 mL) was added triphenylphosphine (26 g, 99 mmol), followed by benzoic acid (10.1 g, 82.7 mmol) and DEAD (9.5 mL, 60 mmol). The reaction mixture was stirred at RT for 2 hours, then partitioned between water and $CH_2Cl_2$. The organic phase was washed with saturated aqueous $NaHCO_3$ and brine, dried over $Na_2SO_4$ and filtered. The filtrate was concentrated under reduced pressure to give a crude product, which was chromatographed (silica gel) eluting with 15% EtOAc/hexane to give 18.1 g of the title compound as a colorless oil.

7C. (2S,3R)-N-tert-Butoxycarbonyl-3-hydroxy-2-pyrrolidinecarboxylic acid methyl ester

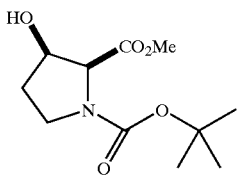

To a solution of 7B (18 g, 51.5 mmol) in anhydrous MeOH (360 mL) at RT was slowly added a freshly prepared 1N solution of KOH in anhydrous MeOH (77 mL, 77 mmol) in portions. The mixture was stirred at RT until the reaction was completed (about 1 hour). The reaction was cooled at 0° C., then quenched by slow addition of 1N aqueous HCl (77 mL). The mixture was concentrated under reduced pressure to remove most of the MeOH solvent, and the remaining mixture partitioned between water and EtOAc. The separated EtOAc phase was washed with saturated aqueous NaHCO$_3$ and brine, dried over Na$_2$SO$_4$ and filtered. The filtrate was concentrated under reduced pressure to give a crude product, which was chromatographed eluting with 30% EtOAc/hexane to give 12.4 g of the title compound as a colorless oil.

7D. (2S,3R)-3-Hydroxy-2-pyrrolidinecarboxylic acid methyl ester, trifluoroacetic acid salt

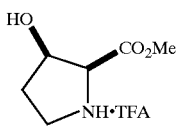

To a solution of 7D (12 g, 48.8 mmol) in CH$_2$Cl$_2$ (300 mL) cooled at 0° C. was added TFA (60 mL). After stirring at 0° C. for 30 min, additional amount of TFA (30 mL) was added. The mixture was allowed to stir at 0° C. for an additional 1 h, then concentrated and the oily residue stripped with diethylether (2×) under reduced pressure and dried in vacuo to give a white foam.

7E. (2S,3R)-3-Hydroxy-2-pyrrolidinecarboxylic acid methyl ester

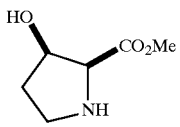

To a solution of 7D (48.8 mmol) in MeOH (120 mL) was added Diaion® WA21J resin (70 g). The resulting suspension was stirred at room temperature for 20 min, and then filtered. The filtrate was concentrated carefully under reduced pressure to give the title compound (7.7 g) as a colorless oil.

7F. (2S,3R)-1-(4-Cyano-naphthalen-1-ylcarbamoyl)-3-hydroxy-pyrrolidine-2carboxylic acid methyl ester

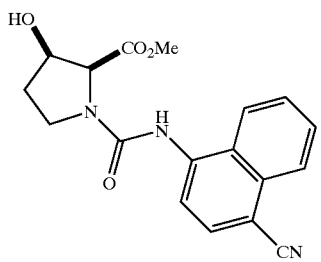

To a solution of 7D (510 mg, 1.97 mmol) in CH$_2$Cl$_2$ (10 mL) cooled at 0° C. was added N,N-diisopropylethylamine (0.35 mL, 2 mmol) and the mixture was stirred at RT for 20 min, then 6B (345 mg, 1.785 mmol) was added. After stirring for 30 min, the reaction was partitioned between CH$_2$Cl$_2$ and saturated aqueous NH$_4$Cl. The CH$_2$Cl$_2$ phase was washed with brine, dried over Na$_2$SO$_4$ and filtered. The filtrate was concentrated under reduced pressure to give a crude product, which was chromatographed (silica gel) eluting with 0.5% MeOH in EtOAc/hexane (1:1) to give 436 mg of the title compound as a white foam. MS (ES): m/z 340 [M+1]$^+$.

7G. (7R,7αS)-4-(Tetrahydro-7-hydroxy-1,3-dioxo-1H-pyrrolo[1,2-c]imidazol-2(3H)-yl)-1-naphthalenecarbonitrile The title compound can also be prepared directly from 7E in an one-pot reaction as described below.

To a suspension of the compound 6B (10.67 g, 55 mmol) in toluene (500 mL) was added compound, 7E (7.7 g, 53 mmol), along with 4 Å molecular sieves (~20 g), the resulting mixture was stirred at RT until formation of 7F was completed. To the mixture was added additional 400 mL of toluene, followed by DBU (6.8 mL, 45.5 mmol), the resulting brown colored suspension was vigorously stirred at RT until the reaction was completed (3 hours). The reaction mixture was loaded on a silica gel column, then eluted with 30% EtOAc/hexane, 50% EtOAc/hexane, and 5% MeOH in EtOAc/hexane (1:1) to give 8.6 g of 7G as an off-white solid (optical purity=98%), which was crystallized from isopropanol to yield 7.35 g of the title compound with 99.8% optical purity. mp. 235–237 C.°; $[\alpha]_D^{rt}=-31$; HPLC: 99% at 12.45 min (retention time) (CHIRALPAK® OD column 4.6×250 mm; 30% isopropanol in hexane over 20 minutes, 1 mL/min, monitoring at 220 nM); MS (ES): m/z 308 [M+1]$^+$.

EXAMPLE 8

(7S,7αR)-4-(Tetrahydro-7-hydroxy-1,3-dioxo-1H-pyrrolo[1,2-c]imidazol- 2(3H)-yl)-1-naphthalenecarbonitrile

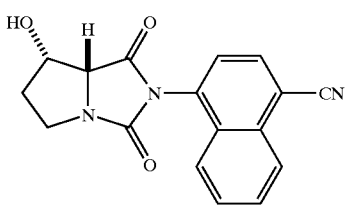

The title compound (1.47 g) was isolated from 6C (5.8 g) by using preparative HPLC with a chiral column (CHIRALPAK® AD, 5×50 cm, 20μ) and 25% of isopropanol/hexane as an eluate. mp. 237–238° C.; $[\alpha]_D^{rt}$=+29.76; HPLC: 99% at 10.77 min (retention time) (CHIRALPAK® OD column 4.6×250 mm; 30% isopropanol in hexane over 20 minutes, 1 mL/min, monitoring at 220 nM); MS (ES): m/z 308 [M+1]⁺.

EXAMPLE 9 trans-Tetrahydro-7-hydroxy-2-(4-nitro-1-naphthalenyl)-1H-pyrrolo[1.2-c]imidazole-1,3(2H)-dione

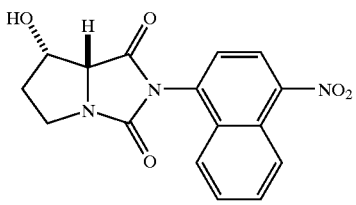

The title compound (racemate) was prepared from 1A and 6A by the procedures analogous to those described in Example 6C. mp. 255–257° C.; HPLC: 99% at 2.13 to 2.27 min (retention time) (YMC S5 ODS column 4.6×50 mm; 10–90% aqueous methanol over 4 minutes containing 0.2% phosphoric acid, 4mL/min, monitoring at 220 nM), MS (ES): m/z 328 [M+1]⁺.

EXAMPLE 10

(7S,7αR)-Tetrahydro-7-hydroxy-2-(4-nitro-1-naphthalenyl)-1H-pyrrolo[1,2-c]imidazole-1,3(2H)-dione

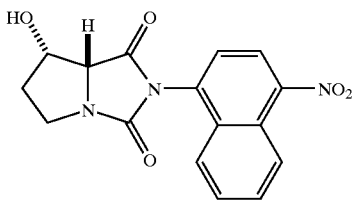

34.8 mg of the tile compound was separated from 80 mg of compound 9 by using preparative HPLC with a chiral column (CHIRALPAK® AD, 5×50 cm, 20μ) and 25% of isopropanol/hexane as an eluate. mp. 253–255 C.°; HPLC: 99% at 14.95 min (retention time) (CHIRALPAK® AD column 4.6×250 mm; 25% isopropanol in hexane over 20 minutes, 1 mL/min, monitoring at 220 nM); MS (ES): m/z 328 [M+1]⁺

EXAMPLE 11

(7R,7αS)-Tetrahydro-7-hydroxy-2-(4-nitro-1-naphthalenyl)-1H-pyrrolo[1,2-c]imidazole-1,3(2H)-dione

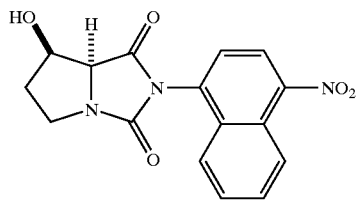

21 mg of the tile compound was separated from 80 mg of compound 9 by using preparative HPLC with a chiral column (CHIRALPAK® AD, 5×50 cm, 20μ) and 25% of isopropanol/hexane as an eluate. mp. 234–236 C.°; HPLC: 99% at 17.79 min (retention time) (CHIRALPAK® AD column 4.6×250 mm; 25% isopropanol in hexane over 20 minutes, 1 mL/min, monitoring at 220 nM); MS (ES): m/z 328 [M+1]⁺.

EXAMPLE 12 trans-2-(4-Bromo-1-naphthalenyl)tetrahydro-7-hydroxy-1H-pyrrolo [1,2-c]imidazole-1,3(2H)-dione

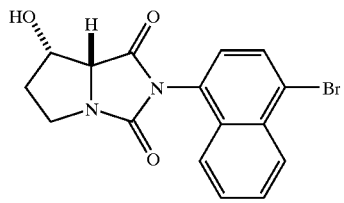

12A. 4-Bromo-1-naphthaleneisocyanate

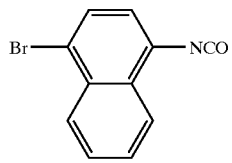

Compound 12A was prepared from 1-amino-4-bromonaphthalene in a similar fashion to that described in Example 1A.

12B. trans-2-(4-Bromo-1-naphthalenyl)tetrahydro-7-hydroxy-1H-pyrrolo [1,2-c]imidazole-1,3(2H)-dione

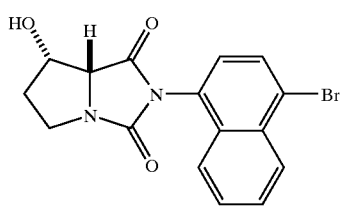

Compound 12B (racemate) was prepared from 6A and 12A by procedures analogous to those described in Example 6C. mp. 204–206 C.°; HPLC: 99% at 2.57–2.65 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 362 [M+1]$^+$.

EXAMPLE 13 trans-4-(Tetrahydro-7-hydroxy-1,3-dioxo-1H-pyrrolo[1,2-c]imidazol-2(3H)-yl)-1-naphthalenecarboxylic acid methyl ester

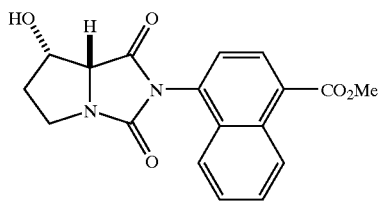

13A. 4-Nitro-1-naphthyldiazonium tetrafluoroborate salt

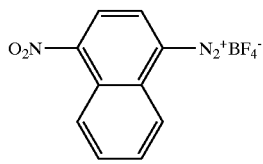

To boron trifluorodiethyletherate (0.51 mL, 4.0 mmol) cooled at −20 C.° was slowly added 1-amine-4-nitronaphthalene (500 mg, 3.0 mmol) in dimethoxy-ethylene (10 mL) over 10 minutes, followed by addition of tert-butylnitrite (0.42 mL, 3.55 mmol) over 1 minute. After addition, the reaction mixture was stirred at −20 C.° for 10 minutes, then at 5 C.° for 20 minutes and pentane (40 mL) was added. The resulting suspension was filtered and the collected solid was washed with ether to give the title compound 13A (730 mg).

13B. 4-Nitro-1-naphthalenecarboxylic acid methyl ester

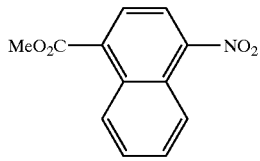

To a suspension of compound 13A (620 mg, 2.16 mmol) in MeOH (50 mL) cooled at 0 C.° under argon was added palladium(II) acetate (24 mg, 0.11 mmol). The reaction vessel was then charged with carbon monoxide gas. The reaction mixture was stirred at 0 C.°, then at RT. The resulting homogenous reaction was quenched with water, extracted with CH$_2$Cl$_2$. The organic layer was separated, washed with brine, dried over Na$_2$SO$_4$ and concentrated under reduced pressure to provide a crude product, which was chromatographed (silica gel) eluting with 2% EtOAc/hexane to give compound 13B (150 mg).

13C. 4-Amino-1-naphthalenecarboxylic acid methyl ester

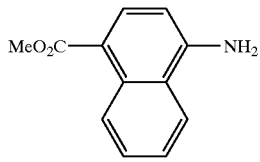

Compound 13B (92 mg, 0.398 mmol) and 10% Pd/C (10 mg) in MeOH (5 mL) was hydrogenated under a hydrogen balloon for 30 minutes. The mixture was filtered and the filtrate concentrated under reduced pressure to give the title compound (80 mg).

13D. 4-Isocyano-1-naphthalenecarboxylic acid methyl ester

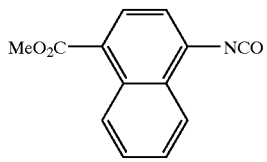

Compound 13D was prepared from 13C by procedures analogous to those described in Example 1A.

13E: trans-4-(Tetrahydro-7-hydroxy-1,3-dioxo-1H-pyrrolo[1,2-c]imidazol-2(3H)-yl)-1-naphthalenecarboxylic acid methyl ester The title compound (racemate) was prepared from 13D by procedures analogous to those described in Example 6C. HPLC: 99% at 2.09–2.27 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 341 [M+1]⁺

EXAMPLE 14 trans-4-(Tetrahydro-7-methoxy-1,3-dioxo-1H-pyrrolo[1,2-c]imidazol-2(3H)-yl)-1-naphthalenecarbonitrile

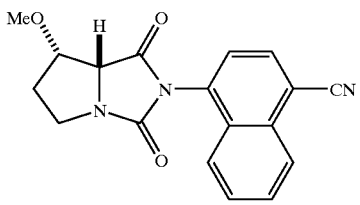

To a solution of compound 6C (100 mg, 0.326 mmol) in acetonitrile (2 mL), at RT, was added iodomethane (86 μL, 1.38 mmol), followed by silver(I) oxide (42 mg, 0.18 mmol). The mixture was refluxed at 85 C.° for 16 hours. After cooling to RT, the reaction mixture was filtered and the filtrate was concentrated under reduced pressure to give a crude product, which was purified by using a preparative HPLC (gradient, 20 to 90% of MeOH /H$_2$O containing 0.1% of CF$_3$CO$_2$H over 10 minutes) to yield the title compound (racemate) (72 mg, 69% yield) as an off-white solid. mp. 185–186 C.°. HPLC: 99% at 2.45 min (retention time) (YMC S5 ODS column 4.6×50 mm; 10–90% aqueous methanol over 4 minutes containing 0.2% phosphoric acid, 4 mL/min, monitoring at 220 nM), MS (ES): m/z 322 [M+1]⁺.

EXAMPLE 15

4-(7-Acetoxy-1,3-dioxo-tetrahydro-pyrrolo[1,2-c]imidazol-2-yl)-naphthalene-1-carbonitrile

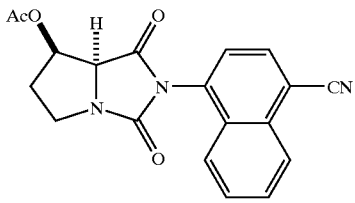

To a solution of 6C (123 mg, 0.4 mmol) in pyridine (3 mL) was added acetic anhydride (0.26 mL, 2.8 mmol), followed by 4-dimethylaminopyridine (15 mg). The reaction mixture was stirred at RT for 3 h, then quenched with water and extracted with CH$_2$Cl$_2$ (3×10 mL). The combined organic extracts were washed with brine, dried over Na$_2$SO$_4$ and filtered. The filtrate was concentrated under reduced pressure to give a crude product, which was chromatographed (silica gel) eluting with 2% MeOH in EtOAc/hexane (1:1) to give 70 mg of the title compound (racemate) as a white solid. m.p. 105 C.°; HPLC: 99% at 4.8 min (retention time) (Conditions: Zorbax SB C18 (4.6×75 mm); Eluted with 0% to 100% B, 8 min gradient. (A=90% H$_2$O-10% MeOH-0.1% H$_3$PO$_4$ and B=10% H$_2$O-90% MeOH-0.1% H$_3$PO$_4$); Flow rate at 2.5 mL/min. UV detection at 220 nm). MS (ES): m/z 350 [M+1]⁺.

EXAMPLE 16

4-(7-Fluoro-1,3-dioxo-tetrahydro-pyrrolo[1,2-c]imidazol-2-yl)-naphthalene-1-carbonitrile

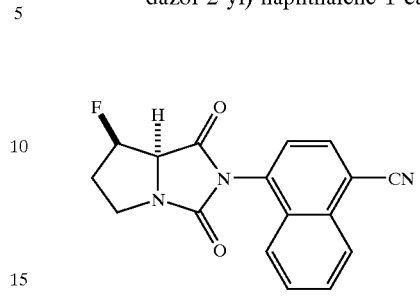

To a solution of diethylaminosulfur trifluoride (0.073 mL, 0.45 mmol) in CH$_2$Cl$_2$ (2 mL) cooled at –78° C. in a flame-dried flask under argon was added dropwise a solution of 6C (92 mg, 0.3 mmol) in CH$_2$Cl$_2$ (12 mL). After addition, the reaction mixture was stirred at –78° C. for 30 min, then at 0° C. overnight. The reaction mixture was partitioned between CH$_2$Cl$_2$ and saturated aqueous NaHCO$_3$. The separated aqueous layer was extracted with CH$_2$Cl$_2$ (2×). The combined CH$_2$Cl$_2$ layers were washed with brine, dried over Na$_2$SO$_4$ and filtered. The filtrate was concentrated under reduced pressure to give a crude product, which was chromatographed (silica gel) eluting with EtOAc/hexane (1:2) to give 52 mg of the title compound (racemate) as a white solid. m.p. 228–230 C.°; HPLC: 99% at 5.0 min (retention time) (Conditions: Zorbax SB C18 (4.6×75 mm); Eluted with 0% to 100% B, 8 min gradient. (A=90% H$_2$O-10% MeOH-0.1% H$_3$PO$_4$ and B=10% H$_2$O-90% MeOH-0.1% H$_3$PO$_4$); Flow rate at 2.5 mL/min. UV detection at 220 nm). MS (ES): m/z 641 [2M+Na]⁺.

EXAMPLE 17

(4-(5,7-Dioxo-dihydro-imidazo[1,5-c]thiazol-6-yl)-naphthalene-1-carbonitrile

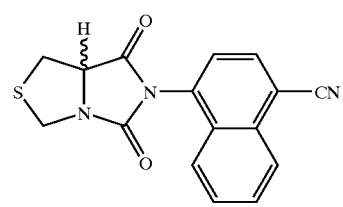

17A. Thiazolidine-4-carboxylic acid methyl ester

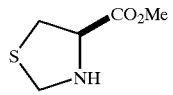

Hydrogen chloride gas was bubbled through a suspension of L-thioproline (990 mg, 7.55 mmol) in MeOH (30 mL) cooled at 0° C. for 5 min. The resulting clear solution was stirred at RT for 2 h, then concentrated carefully under reduced pressure. The obtained residue was dried in vacuo overnight to give a white solid, which was dissolved in MeOH (30 mL) and treated with Diaion® WA21J resin (6 g). The resulting suspension was stirred at RT for 30 min, then filtered. The filtrate was concentrated carefully under reduced pressure and the oily residue stripped with toluene (2×) to give a colorless oil.

17B. (4-(5,7-Dioxo-dihydro-imidazo[1,5-c]thiazol-6-yl)-naphthalene-1-carbonitrile To a suspension of 17A (1.1 g, 7.6 mmol) and 4 Å molecular sieves (5 g) in toluene (40 mL) under argon was added a solution of 6B (1.47 g, 76 mmol) in toluene (20 mL). After addition, the reaction mixture was stirred at RT overnight, then DBU (1.05 mL, 7.55 mmol) was added. The resulting dark red solution was stirred at 80° C. for 3 h. After cooling to RT, the reaction mixture was partitioned between $CH_2Cl_2$ and $H_2O$. The organic phase was washed with brine, dried over $Na_2SO_4$ and filtered. The filtrate was concentrated under reduced pressure to give a yellowish residue, which was chromatographed (silica gel) eluting with EtOAc/hexane (4:7) to give 226 mg of the title compound (racemate) as a white solid. m.p. 223–225 C.°; HPLC: 99% at 5.2 min (retention time) (Conditions: Zorbax SB C18 (4.6×75 mm); Eluted with 0% to 100% B, 8 min gradient. (A=90% $H_2O$-10% MeOH-0.1% $H_3PO_4$ and B=10% $H_2O$-90% MeOH-0.1% $H_3PO_4$); Flow rate at 2.5 mL/min. UV detection at 220 nm). MS (ES): m/z 641 $[2M+Na]^+$.

EXAMPLE 18

4-(2,5,7-Trioxo-dihydro-imidazo[1,5-c]thiazol-6-yl)-naphthalene-1-carbonitrile

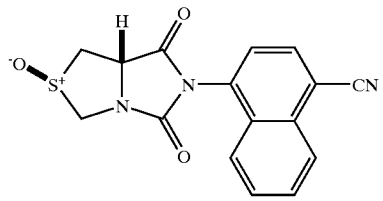

To a solution of 17B (62 mg, 0.2 mmol) in $CH_2Cl_2$ (1.5 mL) was added 3chloroperoxybenzoic acid (46 mg, 0.2 mmol). The reaction was stirred at RT for 2 h, then quenched with 5% aqueous $Na_2S_2O_3$ and extracted with $CH_2Cl_2$ (2×) and EtOAc (2×). The combined organic extracts were washed with saturated aqueous $NaHCO_3$, brine, dried over $Na_2SO_4$ and filtered. The filtrate was concentrated under reduced pressure to give a crude product, which was chromatographed (silica gel) eluting with EtOAc/hexane (2:3) to give 6 mg of the title compound (reacemate) as a white solid. HPLC: 97% at 4.0 min (retention time) (Conditions: Zorbax SB C18 (4.6×75 mm); Eluted with 0% to 100% B, 8 min gradient. (A=90% $H_2O$-10% MeOH-0.1% $H_3PO_4$ and B=10% $H_2O$-90% MeOH-0.1% $H_3PO_4$); Flow rate at 2.5 mL/min. UV detection at 220 nm). MS (ES): m/z 326 $[M+1]^+$.

EXAMPLE 19

4-(2,5,7-Trioxo-dihydro-imidazo[1,5-c]thiazol-6-yl)-naphthalene-1-carbonitrile (racemate)

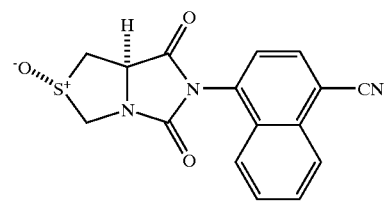

The crude product from Example 18 was chromatographed (silica gel) eluting with EtOAc/hexane (2:3) to give 20 mg of the title compound (racemate) as a white solid. HPLC: 96% at 3.9 min (retention time) (Conditions: Zorbax SB C18 (4.6×75 mm); Eluted with 0% to 100% B, 8 min gradient. (A=90% $H_2O$-10% MeOH-0.1% $H_3PO_4$ and B=10% $H_2O$-90% MeOH-0.1% $H_3PO_4$); Flow rate at 2.5 mL/min. UV detection at 220 nm). MS (ES): m/z 326 $[M+1]^+$.

EXAMPLE 20

4-(1,3-Dioxo-5,6-dihydro-1H-pyrrolo[1,2-c]imidazol-2-yl)-naphthalene-1-carbonitrile

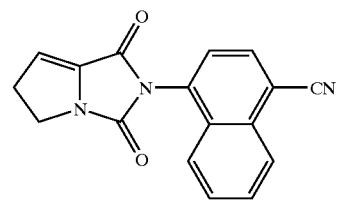

To a suspension of compound 8 (200 mg, 0.65 mmol) in $CH_2Cl_2$ (3 mL) was added pyridine (0.06 mL), followed by triflic anhydride (0.12 mL, 0.71 mmol) and 4dimethylaminopyridine (5 mg). The reaction was stirred at RT for 15 min and the resulting reddish clear solution was treated with DBU (0.1 mL, 0.71 mmol). The mixture was stirred at RT for 30 min, then quenched with saturated aqueous $NH_4Cl$ solution and extracted with $CH_2Cl_2$ (3×). The combined extracts were washed with $H_2O$, brine, dried over $Na_2SO_4$ and filtered. The filtrate was concentrated under reduced pressure to give a crude product, which was chromatographed (silica gel) eluting with EtOAc/hexane (1:1) to give 150 mg of the title compound as an off-white solid. m.p. 230–232° C. HPLC: 99% at 2.43 min (retention time) (Conditions: YMC. S5 ODS column (4.6×50 mm); Eluted with 0% to 100% B, 4 min gradient. (A=90% $H_2O$-10% MeOH-0.1% $H_3PO_4$ and B=10% $H_2O$-90% MeOH-0.1% $H_3PO_4$); Flow rate at 4 mL/min. UV detection at 220 nm). MS (ES): m/z 290 $[M+1]^+$.

EXAMPLE 21

(7αS)-4-(1,3-Dioxo-5,7a-dihydro-1H-pyrrolo[1,2-c]imidazol-2-yl)-naphthalene-1-carbonitrile

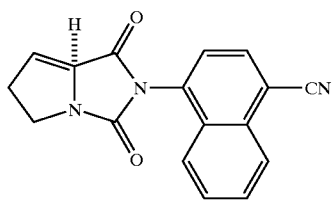

21A. 3,4-Dehydro-L-proline methyl ester, trifluoroacetic acid salt

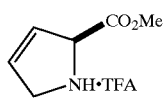

To a solution of N-Boc-3,4-dehydro-L-proline methyl ester (Peninsula Labs) (1 g, 4.405 mmol) in $CH_2Cl_2$ (3 mL) cooled at 0° C. was added TFA (2 mL). After addition, the reaction mixture was stirred at RT for 1 h, then concentrated under reduced pressure to give an oily residue, which was stripped with ether (2×) and dried in vacuo to give a colorless oil (954 mg).

21B. (7αS)-4-(1,3-Dioxo-5,7a-dihydro-1H-pyrrolo[1,2-c]imidazol-2-yl)-naphthalene-1-carbonitrile To a solution of 21A (0.17 g, 0.75 mmol) in $CH_2Cl_2$ (5 mL) was added N,N-diisopropylethylamine (0.135 mL, 0.77 mmol), followed by a solution of 6B (115 mg, 0.595 mmol) in $CH_2Cl_2$ (5 mL) and 4 Å molecular sieves (2 g). After stirring at RT for 3 h, DBU (0.1 mL, 0.65 mmol) was added, followed by toluene (10 mL) and the reaction mixture was heated at 75° C. for 6 h. After cooling to RT, the reaction mixture was partitioned between saturated aqueous $NH_4Cl$ and $CH_2Cl_2$. The organic layer was washed with brine, dried over $Na_2SO_4$ and filtered. The filtrate was concentrated under reduced pressure to give a crude product, which was chromatographed (silica gel) eluting with 30% EtOAc/hexane to give a racemic product. The title compound (37 mg) was isolated by using preparative HPLC with a chiral column (CHIRALPAK® AD, 5×50 cm, 20μ) and 40% of isopropanol/hexane as an eluate. HPLC: 99% at 19.4 min (retention time) (CHIRALPAK® AD column 4.6×250 mm; 35% isopropanol in hexane over 30 minutes, 1 mL/min, monitoring at 220 nM); MS (ES): m/z 290 $[M+1]^+$.

EXAMPLE 22

(7αR)-4-(1,3-Dioxo-5,7a-dihydro-1H-pyrrolo[1,2-c]imidazol-2-yl)-naphthalene-1-carbonitrile

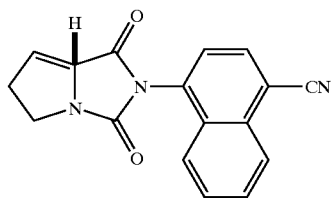

The title compound (46 mg) was isolated from the racemate prepareded in Example 21 by using preparative HPLC with a chiral column (CHIRALPAK® AD, 5×50 cm, 20μ) and 40% of isopropanol/hexane as an eluate. HPLC: 99% at 13.2 min (retention time) (CHIRALPAK® AD column 4.6×250 mm; 35% isopropanol in hexane over 30 minutes, 1 mL/min, monitoring at 220 nM); MS (ES): m/z 290 $[M+1]^+$.

EXAMPLE 23

(7αR)-4-(6,7-Dihydroxy-1,3-dioxo-tetrahydro-pyrrolo[1,2-c]imidazol-2-yl)-naphthalene-1-carbonitrile

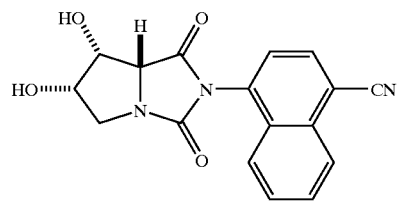

To a solution of compound 22 (50 mg, 0.173 mmol) in acetone/$H_2O$ (5mL/0.2 mL) cooled at 0° C. was added 4-methylmorpholine N-oxide (41 mg, 0.346 mmol), followed by osmium tetraoxide (2.5 wt. % solution in 2-methyl-2-propanol) (0.353 mL, 0.035 mmol). The reaction mixture was stirred at RT overnight, then filtered. The filtrate was concentrated under reduced pressure to give a crude product, which was partitioned between EtOAc and saturated aqueous $NaHCO_3$. The organic layer was washed with brine, dried over $Na_2SO_4$ and filtered. The filtrate was concentrated in vacuo and the residue chromatographed (silica gel) eluting with 10% MeOH in EtOAc/hexane (3:2) to give 44 mg of the title compound (diastereomeric mixture) as a white solid. m.p. 246° C. HPLC: 99% at 2.02 min (retention time) (Conditions: YMC S5 ODS column (4.6×50 mm); Eluted with 0% to 100% B, 4 min gradient. (A=90% $H_2O$-10% MeOH-0.1% $H_3PO_4$ and B=10% $H_2O$-90% MeOH-0.1% $H_3PO_4$); Flow rate at 4 mL/min. UV detection at 220 nm). MS (ES): m/z 324 $[M+1]^+$.

EXAMPLE 24

(7αS)-4-(6,7-Dihydroxy-1,3-dioxo-tetrahydro-pyrrolo[1,2-c]imidazol-2-yl)-naphthalene-1-carbonitrile

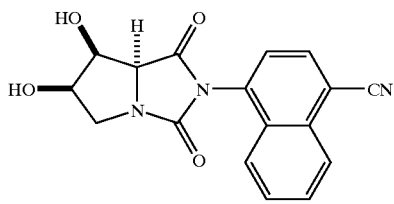

The title compound (diastereomeric mixture) (52 mg) was prepared from compound 21 (50 mg) by the procedures analogous to those described in Example 23. m.p. 225° C. HPLC: 99% at 2.03 min (retention time) (Conditions: YMC S5 ODS column (4.6×50 mm); Eluted with 0% to 100% B, 4 min gradient. (A=90% $H_2O$-10% MeOH-0.1% $H_3PO_4$ and B=10% $H_2O$-90% MeOH-0.1% $H_3PO_4$); Flow rate at 4 mL/min. UV detection at 220 nm). MS (ES): m/z 324 $[M+1]^+$.

EXAMPLE 25

(7S,7αR)-4-(7-Hydroxy-7a-methyl-1,3-dioxo-tetrahydro-pyrrolo[1,2-c]imidazol-2-yl)-naphthalene-1-carbonitrile

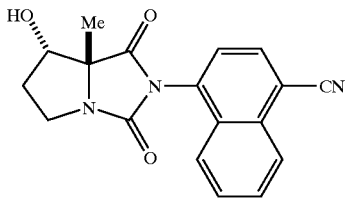

To a stirring suspension of compound 8 (115 mg, 0.374 mmol) in THF (3 mL) at RT under argon was added drops of DMPU. The resulting clear solution was cooled at −78° C., then LDA (2 M solution in THF/heptane/ethylbenzene) (0.37 mL, 0.74 mmol) was added dropwise. The resulting dark brown solution was stirred at −78° C. for 25 min, then iodomethane (0.069 mL, 0.74 mmol) was added. After addition, the reaction mixture was allowed to warm up to −5 to 0° C., and stirred at −5 to 0° C. for 4 h. The reddish colored reaction mixture was quenched with 5% aqueous $KHSO_4$ and extracted with EtOAc (2×20 mL). The combined organic extracts were washed with brine, dried over $Na_2SO_4$ and filtered. The filtrate was concentrated in vacuo and the residue chromatographed (silica gel) eluting with 3% MeOH in EtOAc/hexane (1:1) to give 57 mg of the product, which was further purified using preparative HPLC with a chiral column (CHIRALPAK® AD, 5×50 cm, 20μ) and 20% isopropanol/hexane as an eluate to give 30 mg of the title compound. m.p. 234– 235° C. Chiral HPLC: 99% at 13.9 min (retention time) (CHIRALPAK® AD column 4.6×250 mm; 20% isopropanol in hexane over 30 minutes, 1 mL/min, monitoring at 220 nM); MS (ES): m/z 322 $[M+1]^+$.

EXAMPLE 26

(7R,7αS)-4-(7-Hydroxy-7a-methyl-1,3-dioxo-tetrahydro-pyrrolo[1,2-c]imidazol-2-yl)-naphthalene-1-carbonitrile

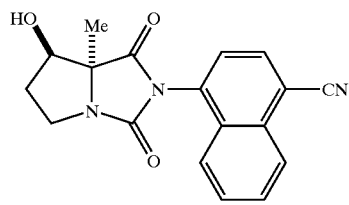

Compound 26 was prepared from 7G by the procedures analogous to those described in Example 25. m.p. 232–234° C. Chiral HPLC: 99% at 24 min (retention time) (CHIRALPAK® AD column 4.6×250 mm; 20% isopropanol in hexane over 30 minutes, 1 mL/min, monitoring at 220 nM); MS (ES): m/z 322 $[M+1]^+$.

EXAMPLE 27

(7R,7αS)-4-(7-Hydroxy-7-methyl-1,3-dioxo-tetrahydro-pyrrolo[1,2-c]imidazol-2-yl)-naphthalene-1-carbonitrile

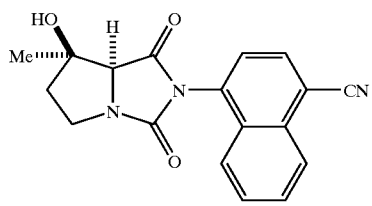

27A.
[tert-Butoxycarbonyl-(3-oxo-butyl)-amino]-acetic acid ethyl ester

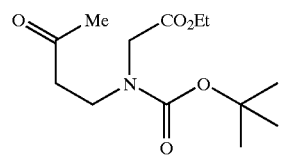

The title compound was prepared by the procedures described in Stocking, E. M.; et al, *J. Am. Chem. Soc.* 122, 1675–1683 (2000).

27B.
3-Hydroxy-3-methyl-pyrrolidine-1,2-dicarboxylic acid 1-tert-butyl ester 2-ethyl ester

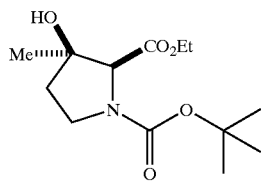

To a solution of 27A (5 g, 18.29 mmol) in toluene (100 mL) cooled at 0° C. was added solid potassium tert-butoxide (2.05 g, 18.29 mmol) in small portions to maintain the solution temperature <5° C. The reaction was stirred at 0° C. for 45 min, then quenched by addition of ice-cooled 10% aqueous $KHSO_4$ solution and extracted with $CH_2Cl_2$ (3×). The combined organic extracts were washed with brine, dried over $Na_2SO_4$ and filtered. The filtrate was concentrated under reduced pressure to give a brown oily residue, which was chromatographed (silica gel) eluting with EtOAc/hexane (1:3) to give 530 mg of the title compound (racemate).

27C. (7R,7αS)-4-(7-Hydroxy-7-methyl-1,3-dioxo-tetrahydro-pyrrolo[1,2-c]imidazol-2-yl)-naphthalene-1-carbonitrile To a solution of 27B (500 mg, 1.83 mmol) in $CH_2Cl_2$ (1.5 mL) was added TFA (1.5 mL). The reaction mixture was stirred at RT for 1 h, then concentrated under reduced pressure to give an oily residue, which was stripped with toluene (3×) and dried in vacuo overnight. The oily residue was dissolved in $CH_2Cl_2$ (10 mL) and to the solution was added N,N-diisopropylethylamine (0.35 mL, 2.01 mmol), followed by a solution of 6B (355 mg, 1.83 mmol) in $CH_2Cl_2$ (5 mL) and 4 Å molecular sieves (1 g). The reaction mixture was stirred at RT for 1 h, the resulting turbid solution (formation of the urea intermediate) was treated with DBU (0.41 mL, 2.745 mmol), and stirred at RT for an additional 1 h. The clear reaction solution was partitioned between $CH_2Cl_2$ and 5% aqueous $KHSO_4$. The aqueous phase was extracted with $CH_2Cl_2$ (2×) and the combined $CH_2Cl_2$ extracts were washed with brine, dried over $Na_2SO_4$ and filtered. The filtrate was concentrated under reduced pressure to give a crude product, which was chromatographed (silica gel) eluting with 4% MeOH in EtOAc/hexane (1:1) to give 330 mg of the desired product as a racemic mixture. The title compound (8 mg) was isolated by using preparative HPLC with a chiral column (CHIRALPAK® AD, 5×50 cm, 20μ) and 10% of isopropanol/hexane as an eluate. Chiral HPLC: 99% at 20.6 min (retention time) (CHIRALPAK® AD column 4.6×250 mm; 20% isopropanol in hexane over 30 minutes, 1 mL/min, monitoring at 220 nM); MS (ES): m/z 322 $[M+1]^+$.

EXAMPLE 28

(7S,7αR)-4-(7-Hydroxy-7-methyl-1,3-dioxo-tetrahydro-pyrrolo[1,2-c]imidazol-2-yl)-naphthalene-1-carbonitrile

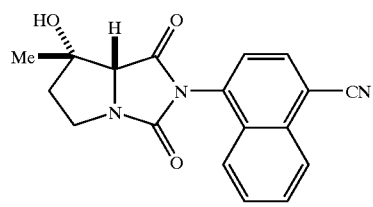

The title compound (7 mg) was isolated from the racemate prepareded in Example 27C by using preparative HPLC with a chiral column (CHIRALPAK® AD, 5×50 cm, 20μ) and 10% of isopropanol/hexane as an eluate. Chiral HPLC: 99% at 23.5 min (retention time) (CHIRALPAK® AD column 4.6×250 mm; 20% isopropanol in hexane over 30 minutes, 1 mL/min, monitoring at 220 nM); MS (ES): m/z 322 $[M+1]^+$.

EXAMPLE 29

(7R,7αS)-4-(7-Hydroxy-1-oxo-3-thioxo-tetrahydro-pyrrolo[1,2-c]imidazol-2-yl)-naphthalene-1-carbonitrile

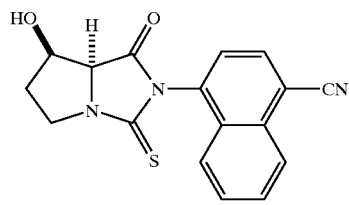

29A. 4-Cyano-N-thionylnaphthylamine

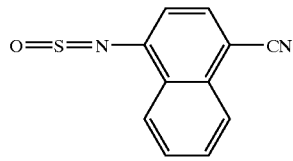

To a suspension of 4-cyano-naphthylamine (200 mg, 1.19 mmol) and $NaHCO_3$ (1 g) in $CHCl_3$ (15 mL) at RT was added thiophosgene (2.36 mL, 30.8 mmol) dropwise. After addition, the reaction mixture was stirred at RT for 4 h, then filtered and the filtrate concentrated in vacuo to dryness to give the title compound as a solid.

29B. (7R,7αS)-4-(7-Hydroxy-1-oxo-3-thioxo-tetrahydro-pyrrolo[1,2-c]imidazol-2-yl)-naphthalene-1-carbonitrile To a solution of 7D (325 mg, 1.25 mmol) in CH$_2$Cl2 (5 mL) was added N,N-diisopropylethylamine (0.32 mL, 1.875 mmol). The reaction mixture was stirred at RT for 30 min, then a solution of 29A in toluene (10 mL) was added. After stirring at RT for 2 h, DBU (0.185 mL, 1.20 mmol) was added and the reaction mixture was stirred for an additional 2 h. The reaction mixture was concentrated in vacuo and the residue chromatographed (silica gel) eluting with 30% EtOAc in hexane to give 267 mg as a white solid, which was further purified using preparative HPLC with a chiral column (CHIRALPAK® AD, 5×50 cm, 20µ) and 30% isopropanol/hexane as an eluate to give 50 mg of the title compound as a white solid. m.p. 215–216° C. Chiral HPLC: 98% at 19.1 min (retention time) (CHIRALPAK® AD column 4.6×250 mm; 30% isopropanol in hexane over 30 minutes, 1 mL/min, monitoring at 220 nM); MS (ES): m/z 324 [M+1]$^+$.

EXAMPLE 30

(3R,7S,7αS)-4-(3-tert-Butyl-7-hydroxy-1-oxo-tetrahydro-pyrrolo[1,2-c]imidazol-2-yl)-naphthalene-1-carbonitrile

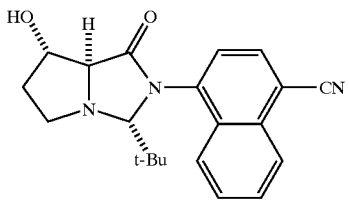

30A. (2S,3S)-3-Hydroxy-pyrrolidine-1,2-dicarboxylic acid 1-tert-butyl ester

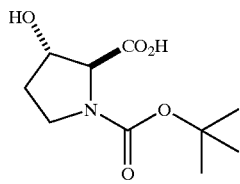

A solution of trans-3-hydroxy-L-proline (9.0 g, 69.2 mmol) in dioxane (94 ml) and water (46 ml) was cooled to 0° C., treated with sodium hydroxide (1.77 g, 44.3 mmol) followed by di-tert-butyl dicarbonate (16.74 g, 7.67 mmol). The mixture was stirred at 0° C. for 5 min, at RT for 6 h then quenched with 2.0 N hydrochloric acid (40 ml, 80 mmol) and extracted with EtOAc (3×350 ml). The combined organic extracts were washed with brine (45 ml) and dried to provide the title compound as a white solid (15.6 g, 97.3%). MS (ES): m/z 254 [M+Na]$^+$.

30B. (2S,3S)-3-(tert-Butyl-dimethyl-silanyloxy)-pyrrolidine-1,2-dicarboxylic acid 1-tert-butyl ester

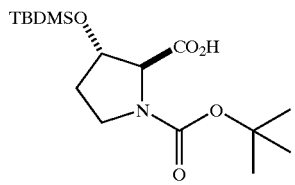

A cooled (0° C.) solution of 30A (15.0 g, 64.8 mmol) and imidazole (22.0 g, 324 mmol) in dry DMF (110 ml) was treated with tert-butyldimethylsilyl chloride (24.3 g, 162 mmol), warmed to RT and stirred for 24 h. The reaction mixture was treated with methanol (150 ml), stirred at RT for another 24 h then partitioned between 10% aqueous citric acid (225 ml) and EtOAc (3×1.0 L). The extracts were washed with brine (200 ml), dried (Na$_2$SO$_4$) and filtered. The filtrate was concentrated to dryness to give a thick colorless syrup (46.0 g). Purification of a portion (20 g) by using automated flash chromatography (135 g silica gel column, EtOAc/hexane gradient) gave the title compound as a thick clear syrup (9.7 g, 99.7%).

30C. (2S,3S)-3-(tert-Butyl-dimethyl-silanyloxy)-2-(4-cyano-naphthalen-1-ylcarbamoyl)-pyrrolidine-1-carboxylic acid tert-butyl ester

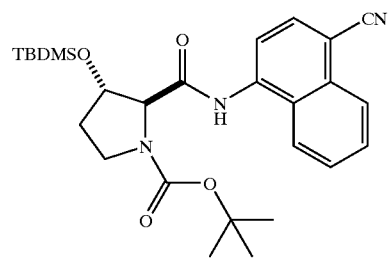

A solution of isobutylchloroformate (0.75 ml, 5.8 mmol) in dry EtOAc (8.0 ml) was cooled to −20° C., treated dropwise with a mixture of 30B (2.0 g, 5.8 mmol) and N-methylmorpholine (0.64 ml, 5.8 mmol) in dry EtOAc (6.0 ml) over a period of 45 minutes. The mixture was stirred at −20° C. for 30 minutes, then treated dropwise over a period of 1.5 h with a solution of 4-aminonaphthalene carbonitrile (976 mg, 5.8 mmol) in dry EtOAc (35 ml). The reaction mixture was stirred at −20° C. for an additional 3.0 h, then at RT for 4 days after which it was partitioned between water (50 ml) and EtOAc (3×250 ml). Purification by flash chromatography provided the title compound as a dark pink foam (2.19 g, 76.3%). MS (ES): m/z 496 [M+1]$^+$.

30D. (2S,3S) 3-Hydroxy-pyrrolidine-2-carboxylic acid (4-cyano-naphthalen-1-yl)-amide

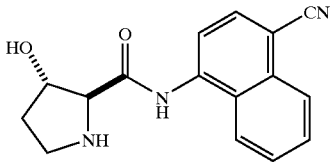

A solution of 30C (700 mg, 1.4 mmol) in dry CH$_2$Cl$_2$ (2.8 ml) and TFA (2.8 ml) was stirred at RT for 4 days. The reaction mixture was diluted with CH$_2$Cl$_2$ (35 ml), concentrated to a syrup and stripped with toluene (35 ml) and ether (2×20 ml). The residual syrup was dissolved in water (7.0 ml), basified with 1.0 N NaHCO$_3$ (5.0 ml) to pH 8.0, extracted with CH$_2$Cl$_2$ (2×100 ml) and the combined organic extracts were dried (Na$_2$SO$_4$) and concentrated. Purification by automated flash chromatography (35 g silica gel column, EtOAc/hexane gradient) gave the title compound as an off-white solid (249 mg, 83.4%), m.p. 174–176° C. MS (ES): m/z 282 [M+1]$^+$.

30E. (3R,7S,7αS)-4-(3-tert-Butyl-7-hydroxy-1-oxo-tetrahydro-pyrrolo[1,2-c]imidazol-2-yl)-naphthalene-1-carbonitrile A suspension of 30D (40 mg, 0.14 mmol) and pivalaldehyde (30 μl, 0.27 mmol) in a mixture of dry benzene (0.5 ml) and dry pentane (5.0 ml) was refluxed for 20 hr with a Dean-Starke receiver, after which additional pivalaldehyde (30 ul, 0.27 mmol), dry benzene (0.5 ml) and catalytic toluenesulfonic acid was added (Ref: Org. Lett. 2 (18) 2781–2783, (2000)). The reaction mixture was refluxed for another 25 hr, evaporated to dryness and dried in vacuo. Purification using automated flash chromatography (10 g silica gel column, EtOAc/hexane gradient) gave the title compound (single diastereoisomer) as a white foam (40 mg, 81.8%). MS (ES): m/z 350 [M+1]$^+$

EXAMPLE 31

(3R,7S,7αS)-4-(7-Hydroxy-1-oxo-3-phenyl-tetrahydro-pyrrolo[1,2-c]imidazol-2-yl)-naphthalene-1-carbonitrile

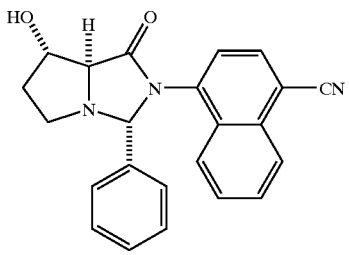

The title compound was obtained from 30D and benzaldehyde in the same manner as described in Example 30E as a cream-colored foam (17.1 mg, 33.1%) by separation on a chiral column (CHIRALPAK® AD, 5×50 cm, 20μ) and 30% isopropanol/hexane as an eluate. MS (ES): m/z 370 [M+1]$^+$.

EXAMPLE 32

(3S,7S,7αS)-4-(7-Hydroxy-1-oxo-3-phenyl-tetrahydro-pyrrolo[1,2-c]imidazol-2-yl)-naphthalene-1-carbonitrile

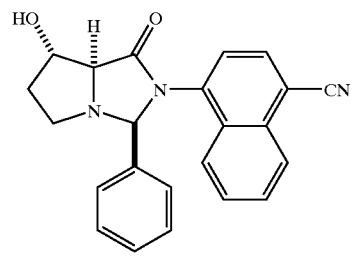

The title compound was obtained from 30D and benzaldehyde in the same manner as described in Example 30E, as an off-white solid (21.8 mg, 42.2%), by separation on a chiral column (CHIRALPAK® AD, 5×50 cm, 20μ) and 30% isopropanol/hexane as an eluate. MS (ES): m/z 370 [M+1]$^+$.

EXAMPLE 33

(3R,6R,7αS)-4-(3-tert-Butyl-6-hydroxy-1-oxo-tetrahydro-pyrrolo[1,2-c]imidazol-2-yl)-naphthalene-1-carbonitrile

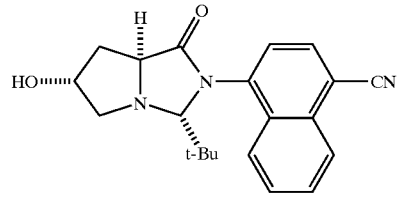

33A. (2S,4R)-4-Benzyloxy-2-(4-cyano-naphthalen-1-ylcarbamoyl)-pyrrolidine-1-carboxylic acid tert-butyl ester

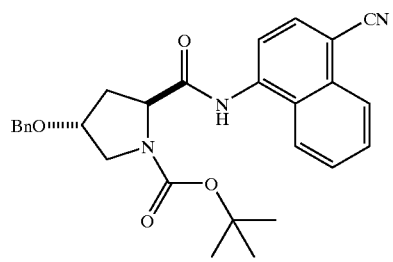

A solution of 1-[tert-butoxy)carbonyl]-4-R-benzyloxy-L-proline (300 mg, 0.934 mmol) in dry THF (8.0 ml) was cooled to −15° C., treated with N-methylmorpholine (0.12 ml, 1.12 mmol) followed by isobutylchloroformate (0.132 ml, 1.03 mmol). The whitish suspension was stirred at −15° C. for 30 min, treated with 4-aminonaphthalene carbonitrile (157.3 mg, 0.934 mmol) and stirred at −15° C. for 30 min then at room temperature for 4 days. (Ref: *J. Med. Chem.*, 33, 635–645, (1998)). The reaction mixture was partitioned between water (7.0 ml) and EtOAc (3×35 ml) and the combined organic extracts washed with brine (7.0 ml) and dried (Na$_2$SO$_4$). Purification using automated flash chromatography (35 g silica gel column, EtOAc/hexane gradient) provided the title compound as a clear syrup (201.7 mg, 45.8 %). MS (ES): m/z 472 [M+1]$^+$.

33B. (2S,4R)-4-Benzyloxy-pyrrolidine-2-carboxylic acid (4-cyano-naphthalen-1-yl)-amide

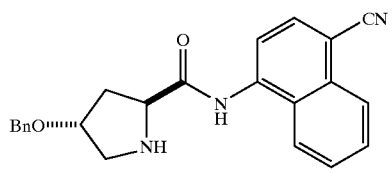

A solution of 33A (201 mg, 0.43 mmol) in dry CH$_2$Cl$_2$ (0.6 ml) and TFA (0.6 ml) was stirred at RT for 40 min. The reaction mixture was diluted with CH$_2$Cl$_2$ (5 ml), concentrated to a syrup and chased with toluene (2×10 ml) and ether (2×50 ml) to give a syrup (202.9 mg).

The residual syrup (185 mg, 0.38 mmol) was dissolved in water (2.0 ml), basified with 1.0 N NaHCO$_3$ (0.45 ml), extracted with CH$_2$Cl$_2$ (2×20 ml) and the combined organic extracts were washed with brine (2.0 ml), dried (Na$_2$SO$_4$) and concentrated in vacuo to give the title compound as a light beige syrup (151 mg, 100 %). MS (ES): m/z 372 [M+1]$^+$.

33C. (3R,6R,7αS)-4-(6-Benzyloxy-3-tert-butyl-1-oxo-tetrahydro-pyrrolo[1,2-c]imidazol-2-yl)-naphthalene-1-carbonitrile

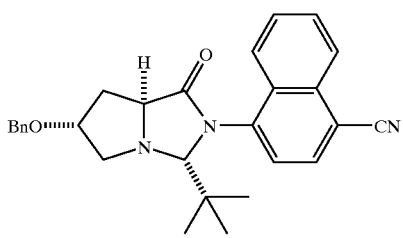

A suspension of 33B (151 mg, 0.38 mmol) and pivalaldehyde (100 μl, 0.90 mmol) in a mixture of dry benzene (0.5 ml) and dry pentane (5.0 ml) was refluxed for 25 hr with a Dean-Starke receiver (Ref: Org. Lett., 2 (18) 2781–2783, (2000)). The reaction mixture was evaporated to dryness and dried in vacuo. Purification using automated flash chromatography (35 g silica gel column, EtOAc/hexane gradient) gave the title compound as a light pink-colored solid (144.1 mg, 86.3%). m.p. 155–157° C. MS (ES): m/z 440 [M+1]$^+$

33D. (3R,6R,7αS)-4-(3-tert-Butyl-6-hydroxy-1-oxo-tetrahydro-pyrrolo[1,2-c]imidazol-2-yl)-naphthalene-1-carbonitrile Compound 33C (94.4 mg, 0.2 mmol) was dissolved in dry CH$_2$Cl$_2$ (5.0 ml), cooled to −75° C., treated with 1.0 M BCl$_3$/CH$_2$Cl$_2$ (1.2 ml, 1.2 mmol) and stirred at −75° C. for 1.5 hr. The reaction mixture was quenched with ice-water (3.4 ml), warmed to room temperature, stirred for 5 min then extracted with CH$_2$Cl$_2$ (50 ml). The organic phase was washed with water (3.4 ml) and brine (3.4 ml) and dried (Na$_2$SO$_4$). Purification using automated flash chromatography (35 g silica gel column, EtOAc/hexane gradient) gave the title compound as a white solid (34.7 mg, 49.6%), m.p. 155–157° C. MS (ES): m/z 350[M+1]$^+$.

EXAMPLE 34

4-(8-Hydroxy-1,3-dioxo-hexahydro-imidazo[1,5-α] pyridin-2-yl)-naphthalene-1-carbonitrile

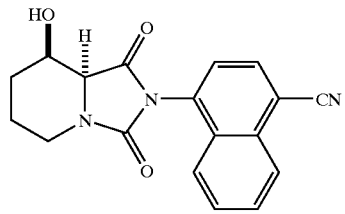

34A. cis-3-Hydroxy-piperidine-2-carboxylic acid

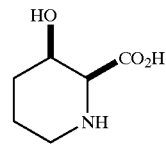

A suspension of 3-hydroxypicolinic acid (1 g, 7.19 mmol) and 5 wt. % rhodium on carbon (200 mg) in a mixed solvents of conc. NH$_4$OH (35 mL) and water (5 mL) in a pressure bottle was stirred under hydrogen at 80 psi overnight. The reaction mixture was filtered and the filtrate concentrated in vacuo to dryness to give 118 mg of the title compound (racemate). MS (ES): m/z 146 [M+1]$^+$.

34B. cis-3-Hydroxy-piperidine-2-carboxylic acid methyl ester; hydrochloride salt

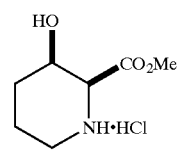

Hydrogen chloride gas was bubbled into a suspension of 34A (1.18 g, 7.19 mmol) in MeOH (100 mL) for 5 min. The resulting clear solution was stirred at RT for 1 h, then concentrated carefully under reduced pressure to give a crude product, which was stripped with toluene (2×) and dried in vacuo to give the title compound (1.4 g).

34C. 4-(8-Hydroxy-1,3-dioxo-hexahydro-imidazo[1,5-α]pyridin-2-yl)-naphthalene-1-carbonitrile To a suspension of 34B (353 mg, 1.81 mmol) and 4 Å molecular sieves (2 g) in CH$_2$Cl$_2$ (5 mL) was added N,N-diisopropylethylamine (0.32 mL, 1.875 mmol). The reaction mixture was stirred at RT for 30 min, then a solution of 6B (275 mg, 1.41 mmol) in toluene (10 mL) was added. After stirring for 2 h, DBU (0.198 mL, 1.41 mmol) was added and the reaction mixture was stirred at RT overnight. The reaction mixture was partitioned between EtOAc and saturated aqueous NH$_4$Cl solution. The separated organic layer was concentrated in vacuo and the residue chromatographed (silica gel) eluting with EtOAc/hexane (1:1), then 3% MeOH in EtOAc/hexane (1:1) to give 230 mg of the title compound (racemate) as a white solid. mp. 243° C. MS (ES): m/z 322 [M+1]$^+$.

EXAMPLE 35

(8R,8αS)-4-(8-Hydroxy-1,3-dioxo-hexahydro-imidazo[1,5-α]pyridin-2-yl)-naphthalene-1-carbonitrile

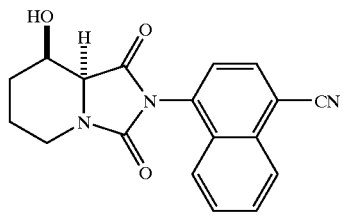

The title compound (31 mg) was isolated from racemic 34C (49 mg) using preparative HPLC with a chiral column (CHIRALPAK® AD, 5×50 cm, 20μ) and 30% isopropanol/hexane as an eluate as a white solid. m.p. 243° C. Chiral HPLC: 99% at 16.5 min (retention time) (CHIRALPAK® AD column 4.6×250 mm; 30% isopropanol in hexane over 30 minutes, 1 mL/min, monitoring at 220 nM); MS (ES): m/z 322 [M+1]$^+$.

EXAMPLE 36

(8S,8αR)-4-(8-Hydroxy-1,3-dioxo-hexahydro-imidazo[1,5-α]pyridin-2-yl)-naphthalene-1-carbonitrile

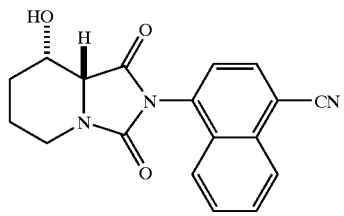

The title compound (12 mg) was isolated from racemic 34C (49 mg) using preparative HPLC with a chiral column (CHIRALPAK® AD, 5×50 cm, 20μ) and 30% isopropanol/hexane as an eluate as a white solid. m.p. 244° C. Chiral HPLC: 99% at 21.1 min (retention time) (CHIRALPAK® AD column 4.6×250 mm; 30% isopropanol in hexane over 30 minutes, 1 mL/min, monitoring at 220 nM); MS (ES): m/z 322 [M+1]$^+$.

EXAMPLE 37

2-(4-Cyano-naphthalen-1-yl)-1,3-dioxo-hexahydro-imidazo[1,5-α]pyrazine-7-carboxylic acid tert-butyl ester

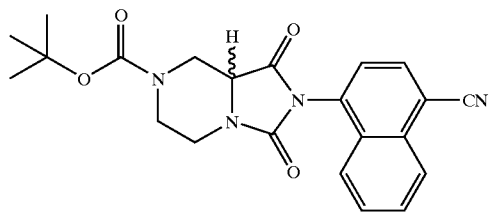

The title compound (930 mg) was prepared from N-4-tert-butoxycarbonyl-2-piperazinecarboxylic acid tert-butyl ester (859 mg) by procedures analogous to those described in Experiment 6C as a white solid. m.p. 222–224° C. Chiral HPLC: 2 peaks at 13.5 min (52%) and 17.6 min (48%) (CHIRALPAK® AS column 4.6×250 mm; 25% isopropanol in hexane over 30 minutes, 1 mL/min, monitoring at 220 nM); MS (ES): m/z 407 [M+1]$^+$.

EXAMPLE 38

4-(1,3-Dioxo-hexahydro-imidazo[1,5-α]pyrazin-2-yl)-naphthalene-1-carbonitrile, hydrochloride salt

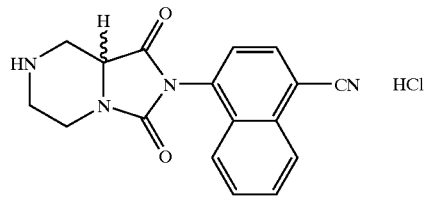

To a solution of 37 (90 mg, 0.22 mmol) in CH$_2$Cl$_2$ (3 mL) was added 4 N HCl/dioxane (0.44 mL, 1.76 mmol). After addition, the reaction mixture was stirred at RT for 2 h and a white precipitate formed. The reaction was filtered and the precipitate was triturated with hexane (2×10 mL). The gummy residue was dissolved in water and lyophilized to give 46 mg of the title compound (racemate) as a white powder.

m.p. 200° C. HPLC: 97% at 2.9 min (retention time) (Conditions: Zorbax SB C18 (4.6×75 mm); Eluted with 0% to 100% B, 8 min gradient. (A=90% H$_2$O-10% MeOH—0.1% H$_3$PO$_4$ and B=10% H$_2$O-90% MeOH-0.1% H$_3$PO$_4$); Flow rate at 2.5 mL/min. UV detection at 220 nm). MS (ES): m/z 307 [M+1]$^+$.

EXAMPLE 39

4-(7-Methanesulfonyl-1,3-dioxo-hexahydro-imidazo[1,5-α]pyrazin-2-yl)-naphthalene-1-carbonitrile

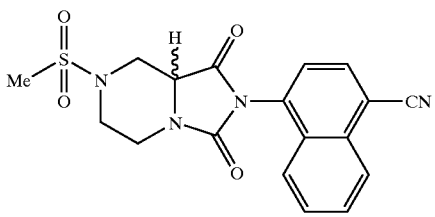

To a solution of 38 (70 mg, 0.164 mmol) in CH$_2$Cl$_2$ (2 mL) at 0° C. was added methanesulfonyl chloride (0.014 mL, 0.18 mmol), followed by Et$_3$N (0.114 mL, 0.82 mmol). After addition, the reaction mixture was stirred at 0–5° C. for 30 min, then loaded on a silica gel cartridge eluting EtOAc/hexane gradient (automated flash chromatography) to give 46 mg of the title compound (racemate) as a white solid.

m.p. 207–216° C. HPLC: 100% at 4.4 min (retention time) (Conditions: Zorbax SB C18 (4.6×75 mm); Eluted with 0% to 100% B, 8 min gradient. (A=90% H$_2$O-10% MeOH-0.1% H$_3$PO$_4$ and B=10% H$_2$O-90% MeOH-0.1% H$_3$PO$_4$); Flow rate at 2.5 mL/min. UV detection at 220 nm). MS (ES): m/z 385 [M+1]$^+$.

EXAMPLE 40

2-(4-Cyano-naphthalen-1-yl)-1,3-dioxo-hexahydro-imidazo[1,5-α]pyrazine-7-carboxylic acid methyl ester

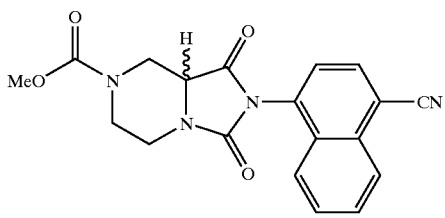

To a solution of 38 (70 mg, 0.164 mmol) in CH$_2$Cl$_2$ (2 mL) at 0° C. was added methyl chloroformate (0.015 mL, 0.2 mmol), followed by Et$_3$N (0.114 mL, 0.82 mmol). After addition, the reaction mixture was stirred at 0–5° C. for 30 min, then loaded on a silica gel cartridge eluting EtOAc/hexane gradient (auto flash chromatography) to give 42 mg of the title compound (racemate) as a white powder. HPLC: 100% at 4.8 min (retention time) (Conditions: Zorbax SB C18 (4.6×75 mm); Eluted with 0% to 100% B, 8 min gradient. (A=90% H$_2$O-10% MeOH-0.1% H$_3$PO$_4$ and B=10% H$_2$O-90% MeOH-0.1% H$_3$PO$_4$); Flow rate at 2.5 mL/min. UV detection at 220 nm). MS (ES): m/z 365 [M+1]$^+$.

EXAMPLE 41

(7R,7αR)-4-(7-Hydroxy-3-oxo-tetrahydropyrrolo[1,2-c]imidazol-2-yl)-naphthalene-1-carbonitrile

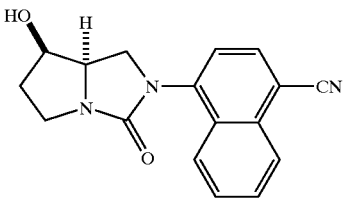

41A. (7R,7αS)-4-(1,7-Dihydroxy-3-oxo-tetrahydropyrrolo[1,2-c]imidazol-2-yl)-naphthalene-1-carbonitrile

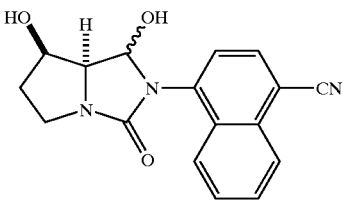

To a suspension of 7G (307 mg, 1.0 mmol) in anhydrous THF (3 mL) at RT was added DMPU (0.5 mL). The resulting solution was cooled at −78° C., then a solution of 1.0 M LiEt$_3$BH/THF (2.5 mL, 2.5 mmol) was added dropwise. After stirring at −78° C. for 1 h, then at 40° C. for 16 h, the reaction mixture was quenched with saturated aqueous NaHCO$_3$ at 40° C. The mixture was stirred at 0° C. for 30 min, then treated with H$_2$O$_2$ and extracted with CH$_2$Cl$_2$ (3×). The combined CH$_2$Cl$_2$ extracts were washed with brine, dried over Na$_2$SO$_4$ and filtered. The filtrate was concentrated under reduced pressure to give a crude product, which was chromatographed (silica gel) eluting with 3–5% MeOH in CH$_2$Cl$_2$ to give the title compound as a white solid (190 mg). MS (ES): m/z 310 [M+1]$^+$.

41B. (7R,7αR)-4-(7-Hydroxy-3-oxo-tetrahydropyrrolo[1,2-c]imidazol-2-yl)-naphthalene-1-carbonitrile To a suspension of 41A (190 mg, 0.615 mmol) in anhydrous CH$_2$Cl$_2$ (3 mL) at RT was added DMPU (0.5 mL). The resulting solution was cooled at −78° C., then Et$_3$SiH (0.8 mL, 5.0 mmol) was added, followed by BF$_3$·Et$_2$O (0.75 mL, 6.0 mmol). The reaction mixture was stirred at −78° C. for 3 h, then at −40° C. overnight. The reaction mixture was quenched with saturated aqueous NaHCO$_3$ at −40° C. The mixture was stirred at RT for 30 min, then extracted with CH$_2$Cl$_2$ (3×). The combined CH$_2$Cl$_2$ extracts were washed with brine, dried over Na$_2$SO$_4$ and filtered. The filtrate was concentrated under reduced pressure to give a crude oily product, which was purified using preparative HPLC to give a white solid (75 mg). The white solid was crystallized from hot isopropyl alcohol to yield the title compound as a white solid (48 mg as a pure single isomer). mp 226–228° C. Chiral HPLC: 99% at 10.20 min (retention time) (CHIRAL- PAK® AD column 4.6×250 mm; 40% isopropanol in hexane over 20 minutes, 1 mL/min, monitoring at 220 nM); MS (ES): m/z 294 [M+1]⁺.

EXAMPLE 42

(7S,7αS)-4-(7-Hydroxy-3-oxo-tetrahydropyrrolo[1,2-c]imidazol-2-yl)-naphthalene-1-carbonitrile

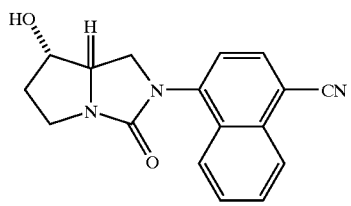

42A. (7S,7αR)-4-(1,7-Dihydroxy-3-oxo-tetrahydropyrrolo[1,2-c]imidazol-2-yl)-naphthalene-1-carbonitrile

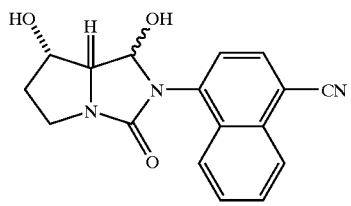

The title compound (176 mg) was prepared from compound 8 (370 mg) by procedures analogous to those described in Example 41A. MS (ES): m/z 310 [M+1]⁺.

42B. (7S,7αS)-4-(7-Hydroxy-3-oxo-tetrahydropyrrolo[1,2-c]imidazol-2-yl)-naphthalene-1-carbonitrile The title compound (40 mg) was prepared from compound 42A (176 mg) by procedures analogous to those described in Example 41B. mp 226–228° C. Chiral HPLC: 99% at 7.36 min (retention time) (CHIRALPAK® AD column 4.6×250 mm; 40% isopropanol in hexane over 20 minutes, 1 mL/min, monitoring at 220 nM); MS (ES): m/z 294 [M+1]⁺.

What is claimed is:

1. A compound of the formula Ia

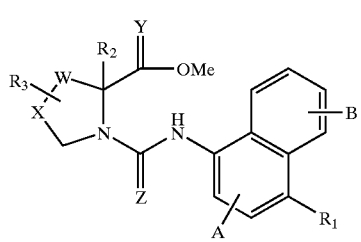

wherein $R_1$ is selected from the group consisting of hydrogen (H), cyano (—CN), nitro (—NO₂), halo, $OR_4$, $CO_2R_5$, $CONHR_5$, $COR_5$, $S(O)_mR_5$, $SO_2NR_5R_5'$, $NHCOR_5$ and $NHSO_2R_5$;

$R_2$ is selected from the group consisting of hydrogen (H), alkyl or substituted alkyl, alkenyl or substituted alkenyl, arylalkyl or substituted arylalkyl, $CO_2R_5$, $CONR_5R_5'$ and $CH_2OR_5$;

$R_3$ is selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, halo, cyano(—CN), $NHCOR_5$, $NHCO_2R_5$, $NHCONR_5R_5'$, $NHSO_2R_5$ and $OR_4$;

$R_4$ in each functional group is independently selected from the group consisting of hydrogen (H), alkyl or substituted alkyl, $CHF_2$, $CF_3$ and $COR_5$;

$R_5$ and $R_5'$ in each functional group are each independently selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and —CN;

W is selected from the group consisting of $(CR_6R_6')_m$, $CHOH(CR_6R_6')_m$, $CO(CR_6R_6')_m$ and $C=NOR_4(CR_6R_6')_m$;

$R_6$ and $R_6'$ are each independently selected from the group consisting of hydrogen (H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, halo, cyano (—CN), $NHCOR_5$, $NHCO_2R_5$, $NHCONR_5R_5'$, $NHSO_2R_5$ and $OR_4$;

X is selected from the group consisting of methylene (—CH₂—);

Y is selected from the group consisting of oxygen(O), sulfur(S) and hydrogen (H₂);

Z is selected from the group consisting of oxygen(O), sulfur(S), NH and $NR_5$;

A and B are each independently selected from the group consisting of hydrogen (H), halo, cyano(—CN), nitro (—NO₂), alkyl or substituted alkyl and $OR_4$; and m is an integer from 0 to 2;

or prodrug esters, pharmaceutically acceptable salts and stereoisomers thereof.

2. A pharmaceutical composition comprising a compound as defined in claim 1.

3. The pharmaceutical composition of claim 2 further comprising at least one additional therapeutic agent selected from the group consisting of parathyroid hormone, bisphosphonates, estrogen, testosterone, progesterone, growth hormone and anti-anxiety agents selected from the group consisting of diazepan, lorazepam, buspirone, oxazepam and hydroxyzine pamoate.

* * * * *